US008883852B2

(12) United States Patent
Epperly et al.

(10) Patent No.: US 8,883,852 B2
(45) Date of Patent: Nov. 11, 2014

(54) RADIOPROTECTIVE AGENTS

(75) Inventors: Michael Epperly, McCandless, PA (US); Joel Greenberger, Sewickley, PA (US); Jianfei Jiang, Pittsburgh, PA (US); Valerian Kagan, Pittsburgh, PA (US); John Lazo, Pittsburgh, PA (US); Peter McDonald, Lawrence, KS (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 664 days.

(21) Appl. No.: 13/124,924

(22) PCT Filed: Oct. 21, 2009

(86) PCT No.: PCT/US2009/061483
§ 371 (c)(1),
(2), (4) Date: Aug. 8, 2011

(87) PCT Pub. No.: WO2010/048287
PCT Pub. Date: Apr. 29, 2010

(65) Prior Publication Data
US 2011/0288178 A1 Nov. 24, 2011

Related U.S. Application Data
(60) Provisional application No. 61/107,394, filed on Oct. 22, 2008.

(51) Int. Cl.
| | |
|---|---|
| A61K 31/64 | (2006.01) |
| A61K 31/17 | (2006.01) |
| A61K 31/4965 | (2006.01) |
| A61K 31/47 | (2006.01) |
| A61K 31/40 | (2006.01) |

(52) U.S. Cl.
CPC .................................... *A61K 31/64* (2013.01)
USPC ...... 514/593; 514/255.06; 514/309; 514/412; 514/423; 514/426

(58) Field of Classification Search
None
See application file for complete search history.

(56) References Cited

U.S. PATENT DOCUMENTS

| | | |
|---|---|---|
| 3,426,067 A | 2/1969 | Weber et al. |
| 3,454,635 A | 7/1969 | Weber et al. |
| 3,507,954 A | 4/1970 | Weber et al. |
| 3,507,961 A | 4/1970 | Weber et al. |
| 4,060,634 A | 11/1977 | Rothe et al. |
| 4,916,163 A | 4/1990 | Ni |
| 6,566,380 B2 | 5/2003 | Reed et al. |
| 6,830,760 B2 | 12/2004 | Cave et al. |
| 6,849,634 B2 | 2/2005 | Beaudoin et al. |
| 6,858,610 B2 | 2/2005 | Gross et al. |
| 2008/0227778 A1 | 9/2008 | Dinsmore et al. |

FOREIGN PATENT DOCUMENTS

WO 2004111057 A1 12/2004

OTHER PUBLICATIONS

Chugh et al., "Glibenclamide vs gliclazide in reducing oxidative stress in patients of noninsulin dependent diabetes mellitus—a double blind randomized study," J. Assoc. Physicians India, Aug. 2001; 49: pp. 803-807—abstract only.*
Amarzguioui, Improved siRNA-mediated silencing in refractory adherent cell lines by detachment and transfection in suspension, BioTechniques, May 2004, 766-770, 36.
Bartz et al., How Will RNAi facilitate Drug Development?, Sciences STKE, Aug. 2, 2005, 1-5, 295.
Busija et al., Mitochondrial-mediated suppression of ROS production upon exposure of neurons to lethal stress: Mitochondrial targeted preconditioning, Adv Drug Deliv Rev, 2008, 1471-1477, 60(13-14).
Chatterjee-Kishore, From genome to phenome—RNAi library screening and hit characterization using signaling pathway analysis, Current Opinion in Drug Discovery & Development, 2006, 231-239, 9-2.
Cox et al., Sulfonylureas and Diabetes Mellitus: I. Clinical Evaluation, Diabetes, Sep.-Oct. 1956, 358-365, 5-5.
Epperly et al., Ascorbate as a "Redox Sensor" and Protector Against Irradiation-Induced Oxidative Stress in 32d CI 3 Hematopoietic Cells and Subclones Overexpressing Human Manganese Superoxide Dismutase, Int. J. Radiation Oncology Biol. Phys., 2004, 851-861, 58-3.
Epperly et al., Bone marrow origin of myofibroblasts in irradiation pulmonary fibrosis, Am. J. Respir. Cell Mol. Biol., 2003, 213-224, 29.
Epperly et al., Ethyl pyruvate, a potentially effective mitigator of damage after total-body irradiation, Radiation Research, 2007, 552-559, 168.
Epperly et al., Manganese Superoxide Dismutase (SOD2) Inhibits Radiation-Induced Apoptosis by Stabiliization of the Mitochondrial Membrane, Radiation Research, 2002, 568-577, 157.
Epperly et al., Mitochondrial Localization of Superoxide Dismutase is Required for Decreasing Radiation-Induced Cellular Damage, Radiation Research, 2003, 568-578, 160.
Epperly et al., Overexpression of the MnSOD transgene product protects cryopreserved bone marrow hematopoietic progenitor cells from ionizing irradiation, Radiation Research, 2007, 560-566, 168.
Epperly et al., Overexpression of the transgene for manganese superoxide dismutase (MnSOD) in 32D cI 3 cells prevents apoptosis induction by Tnf-α, IL-3 withdrawal, and ionizing radiation, Experimental Hematology, 2003, 465-474, 31.
Feldman, Review of glyburide after one year on the market, The American Journal of Medicine, Sep. 20, 1985, 102-108, vol. 79 (suppl 3B).

(Continued)

*Primary Examiner* — Sreeni Padmanabhan
*Assistant Examiner* — Jody Karol
(74) *Attorney, Agent, or Firm* — The Webb Law Firm

(57) ABSTRACT

Provided herein are methods, for reducing, preventing, mitigating and treating damage caused by radiation. The methods comprise delivering a compound, as described herein, to a patient in an amount and dosage regimen effective to prevent, mitigate or treat damage caused by radiation or to mitigate apoptosis. The compounds comprise glyburide or other sulfonylurea hypoglycemic compounds or potassium channel inhibitors.

8 Claims, 10 Drawing Sheets

(56) References Cited

OTHER PUBLICATIONS

Feldman, Glyburide: A Second-generation Sulfonylurea Hypoglycemic Agent, History, Chemistry, Metabolism, Pharmacokinetics, Clinical Use and Adverse Effects, Pharmacotherapy, 1985, 43-62, 5.

Grishin et al., Structure and function of the potassium channel inhibitor from black scorpion venom, Pure & Appl. Chem., 1996, 2105-2109, 68-11.

Hambrock et al., Glibenclamide-induced apoptosis is specifically enhanced by expression of the sulfonylurea receptor isofrom SUR1 but not by expression of SUR2B or the mutant SUR1(M1289T), The Journal of Pharmacology and Experimental Therapeutics, 2006, 1031-1037, 316-3.

Hopkins et al., The druggable genome, Nature Reviews Drug Discovery, Sep. 2002, 727-730, 1.

Hosseinimehr, Foundation review: Trends in the development of radioprotective agents, Drug Discovery Today, Oct. 2007, 794¬ 805, 12-19/20.

Jiang et al., A Mitochondria-Targeted Nitroxide/Hemigramicidin S Conjugate Protects Mouse Embryonic Cells Against Gamma Irradiation, Int J Radiat Oncol Biol Phys, Mar. 1, 2008, 816-825, 70-3.

Johnson et al, Preliminary clinical evaluation of glybenclamide in treatment of diabetes mellitus, Diabetes, Aug. 1970, 579-584, 19.

Kaelin, The concept of synthetic lethality in the context of anticancer therapy, Nature Reviews Cancer, Sep. 2005, 689-698, 5.

Micklem et al., RNAi screening for therapeutic targets in human malignancies, Current Pharmaceutical Biotechnology, 2007, 337-343, 8.

Miura et al., ATP-sensitive K+ channel openers: old drugs with new clinical benefits for the heart, Current Vascular Pharmacology, 2003, 251-258, 1.

Mozaffari et al., Effect of pressure overload on cardioprotection of mitochondrial KATP channels and GSK-3beta: interaction with the MPT pore, American Journal of Hypertension, May 2008, 570-575, 21-5.

Overington et al., How many drug targets are there?, Nature Reviews Drug Discovery, Dec. 2006, 993-996, 5.

Peters et al., Maximal dose glyburide therapy in markedly symptomatic patients with type 2 diabetes: a new use for an old friend, Journal of Clinical Endocrinology and Metabolism, 1996, 2423-2427, 81-7.

Rübel et al., The membrane targeted apoptosis modulators erucylphosphocholine and erucylphosphohomocholine increase the radiation response of human glioblastoma cell lines in vitro, Radiation Oncology, Mar. 24, 2006, 1-17, 1-6.

Simard et al., Drugs acting on SUR1 to treat CNS ischemia and trauma, Curr Opin Pharmacol, Feb. 2008, 42-49, 8-1.

Troy, Remington: The Science and Practice of Pharmacy, 2006, 1452-1456, 21st Edition, Lippincott Williams & Wilkins, Philadelphia.

Tyner et al., RNAi screening of the tyrosine kinome identifies therapeutic targets in acute myeloid leukemia, Blood, Feb. 15, 2008, 2238-2245, 111-4.

Wang, et al., An Ultraviolet-activated K+ Channel Mediates apoptosis of Myeloblastic Leikemia cells, The Journal of Biological Chemistry, Feb. 5, 1999, 3678-3685, 274-6.

Zhang et al., High-content fluorescent-based assay for screening activators of DNA damage checkpoint pathways, Journal of Biomolecular Screening, 2008, 538-543, 13-6.

* cited by examiner

Duplex #1
5'- CCCUACAGUGGAUAGAAGAtt-3'
3'- gtGGGAUGUCACCUAUCUUCU-5'

Duplex #2
5'- GCCGUUCUCAAGGUAUCAAtt-3'
3'- gtCGGCAAGAGUUCCAUAGUU-5'

Duplex #3
5'-GCUACACAUCUUGUCCCAAtt-3'
3'-ctCGAUGUGUAGAACUGGGUU-5'

Glyburide

SEQUENCE LISTING

<160> NUMBER OF SEQ ID NOS: 6

<210> SEQ ID NO 1
<211> LENGTH: 21
<212> TYPE: DNA
<213> ORGANISM: Artificial Sequence
<220> FEATURE:
<223> OTHER INFORMATION: siRNA Duplex #1 - Forward
<220> FEATURE:
<221> NAME/KEY: misc_feature
<223> OTHER INFORMATION: This is a combined DNA/RNA sequence.
<220> FEATURE:
<221> NAME/KEY: misc_feature
<222> LOCATION: (20)..(21)
<223> OTHER INFORMATION: Thymine dimer

<400> SEQUENCE: 1
cccuacagug gauagaagan n                                              21

<210> SEQ ID NO 2
<211> LENGTH: 21
<212> TYPE: DNA
<213> ORGANISM: Artificial Sequence
<220> FEATURE:
<223> OTHER INFORMATION: siRNA Duplex #1 - Reverse
<220> FEATURE:
<221> NAME/KEY: misc_feature
<223> OTHER INFORMATION: This is a combined DNA/RNA sequence.
<220> FEATURE:
<221> NAME/KEY: misc_feature
<222> LOCATION: (20)..(20)
<223> OTHER INFORMATION: Thymine

<400> SEQUENCE: 2
ucuucuaucc acuguauuun g                                              21

<210> SEQ ID NO 3
<211> LENGTH: 21
<212> TYPE: DNA
<213> ORGANISM: Artificial Sequence
<220> FEATURE:
<223> OTHER INFORMATION: siRNA Duplex #2 - Forward
<220> FEATURE:
<221> NAME/KEY: misc_feature
<223> OTHER INFORMATION: This is a combined DNA/RNA sequence.
<220> FEATURE:
<221> NAME/KEY: misc_feature
<222> LOCATION: (20)..(21)
<223> OTHER INFORMATION: Thymine dimer

<400> SEQUENCE: 3
gccguucuca agguaucaan n                                              21

<210> SEQ ID NO 4
<211> LENGTH: 21
<212> TYPE: DNA
<213> ORGANISM: Artificial Sequence
<220> FEATURE:
<223> OTHER INFORMATION: siRNA Duplex #2 - Reverse
<220> FEATURE:
<221> NAME/KEY: misc_feature
<223> OTHER INFORMATION: This is a combined DNA/RNA sequence.
<220> FEATURE:
<221> NAME/KEY: misc_feature
<222> LOCATION: (20)..(20)
<223> OTHER INFORMATION: Thymine

<400> SEQUENCE: 4
uugauaccuu gagaacggcn g                                              21

```
-continued

<210> SEQ ID NO 5
<211> LENGTH: 21
<212> TYPE: DNA
<213> ORGANISM: Artificial Sequence
<220> FEATURE:
<223> OTHER INFORMATION: siRNA Duplex #3 - Forward
<220> FEATURE:
<221> NAME/KEY: misc_feature
<223> OTHER INFORMATION: This is an combined DNA/RNA sequence.
<220> FEATURE:
<221> NAME/KEY: misc_feature
<222> LOCATION: (20)..(21)
<223> OTHER INFORMATION: Thymine dimer

<400> SEQUENCE: 5
gcuacacauc uugucccaan n                                              21

<210> SEQ ID NO 6
<211> LENGTH: 21
<212> TYPE: DNA
<213> ORGANISM: Artificial Sequence
<220> FEATURE:
<223> OTHER INFORMATION: siRNA Duplex #3 - Reverse
<220> FEATURE:
<221> NAME/KEY: misc_feature
<223> OTHER INFORMATION: This is a combined DNA/RNA sequence.
<220> FEATURE:
<221> NAME/KEY: misc_feature
<222> LOCATION: (20)..(20)
<223> OTHER INFORMATION: Thymine

<400> SEQUENCE: 6
uugggucaag auguguagcn c                                              21
```

RADIOPROTECTIVE AGENTS

CROSS REFERENCE TO RELATED APPLICATIONS

This application is a National Stage of International Application No. PCT/US2009/061483, filed Oct. 21, 2009, which in turn claims the benefit of U.S. Provisional Patent Application No. 61/107,394, filed Oct. 22, 2008, which is incorporated herein by reference in its entirety.

The Sequence Listing associated with this application is filed in electronic format via EFS-Web and is hereby incorporated by reference into the specification in its entirety. The name of the text file containing the Sequence Listing is 00020158PCT_ST25.txt. The size of the text file is 2,434 bytes, and the text file was created on Aug. 4, 2011.

STATEMENT REGARDING FEDERAL FUNDING

This invention was made with government support under Grant No. NIAID U19-AI068021 awarded by the National Institutes of Health. The government has certain rights in this invention.

Provided herein are methods of reducing, preventing, or mitigating injury in a subject due to exposure of the subject to radiation, particularly ionizing radiation. The methods include administration to the subject of an amount of a compound effective to prevent, reduce, prevent, or mitigate radiation injury in the patient. The compounds include glyburide as well as other related compounds.

Identification and validation of novel drug targets continues to be a major bottleneck in drug development. The advent of high-throughput analysis of gene function using short interfering RNA (siRNA)-based screens, provides an efficient means to predict novel functions of gene products in cellular signaling pathways and to identify preliminary drug targets. (Chatterjee-Kishore, M. From genome to phenome—RNAi library screening and hit characterization using signaling pathway analysis. Curr. Opin. Drug Discov. Devel. 9, 231-239 (2006) and Bartz, S. & Jackson, A. L. How will RNAi facilitate drug development? *Sci STKE.* 295, 39 (2005).)

The human genome can be divided into those genes encoding proteins that historically have been identified as targets for drugs used for most human diseases; this so called "druggable genome" comprises between 3,000-10,000 genes (Hopkins, A. L. & Groom, C. R. The druggable genome. *Nat. Rev. Drug Discov.* 1, 727-730 (2002) and Overington, J. P., Al-Lazikani, B. & Hopkins, A. L. How many drug targets are there? *Nat. Rev. Drug Discov.* 5, 993-996 (2006).). The products of these genes include protein classes such as kinases, G-protein coupled receptors (GPCRs), phosphatases, proteases, and channels (Hopkins, A. L. & Groom, C. R. The druggable genome. *Nat. Rev. Drug Discov.* 1, 727-730 (2002)). It has been hypothesized that by focusing on the druggable genome, one should increase the likelihood for success of finding good drug targets for human diseases in a drug discovery paradigm. Moreover, screening systems can be established to enable repurposing of clinically used drugs.

The identification and development of effective radioprotectors and mitigators is of considerable importance because of the common application of ionizing radiation (IR) in medical practice, possible accidental exposure to radiation and potential exploitation of radiation by terrorists. Unfortunately, currently there are no approved drugs to prevent acute radiation syndrome, despite extensive exploration (Hosseinimehr, S. J. Trends in the development of radioprotective agents. *Drug Discov. Today* 12, 794805 (2007)).

SUMMARY

We have exploited a human siRNA library targeting the druggable genome to assist in repurposing existing drugs for use as radioprotectors. Using an unbiased 16,560 short interfering RNA library targeting the druggable genome, we performed a synthetic protection screen, which was designed to identify genes that, when silenced, protected human glioblastoma T98G cells from irradiation induced cell death. We identified 116 candidate protective genes. We selected 10 small molecule inhibitors of 13 of these candidate gene products and validated their radioprotective effects. Glyburide, a clinically-used second-generation hypoglycemic drug, effectively relieved irradiation induced cell death in T98G, glioblastoma U-87 MG, normal lung epithelial BEAS-2B, and primary astrocytes. Using a clonogenic assay, we showed that 10 µM glyburide significantly increased the survival of 32D cl 3 murine hematopoietic progenitor cells when administrated 1-h before irradiation (0-8 Gy). Only 33% of C57BL/6NHsd female mice exposed to total body irradiation dose of 9.5Gy survived while 60% of the mice pretreated with an intraperitoneal glyburide dose of 5 mg/kg 10 min before total body irradiation survived. In comparison, 44% of mice injected with glyburide 10-min after irradiation survived. These results demonstrate the power of unbiased siRNA synthetic protection screening with a druggable genome library and suggests compounds that might be clinically useful for radioprotection and for prevention of activation of oxidative stress-induced or DNA damage-induced apoptosis.

BRIEF DESCRIPTION OF THE DRAWINGS

FIG. 3 Silencing of ABCA4 with siRNA duplexes protects T98G cells from γ-irradiation. T98G cells were either transfected with scrambled control siRNA or ABCA4 gene siRNAs. Cells were exposed to 25 Gy γ-irradiation 48 hours after siRNA transfection.

Figure 1:
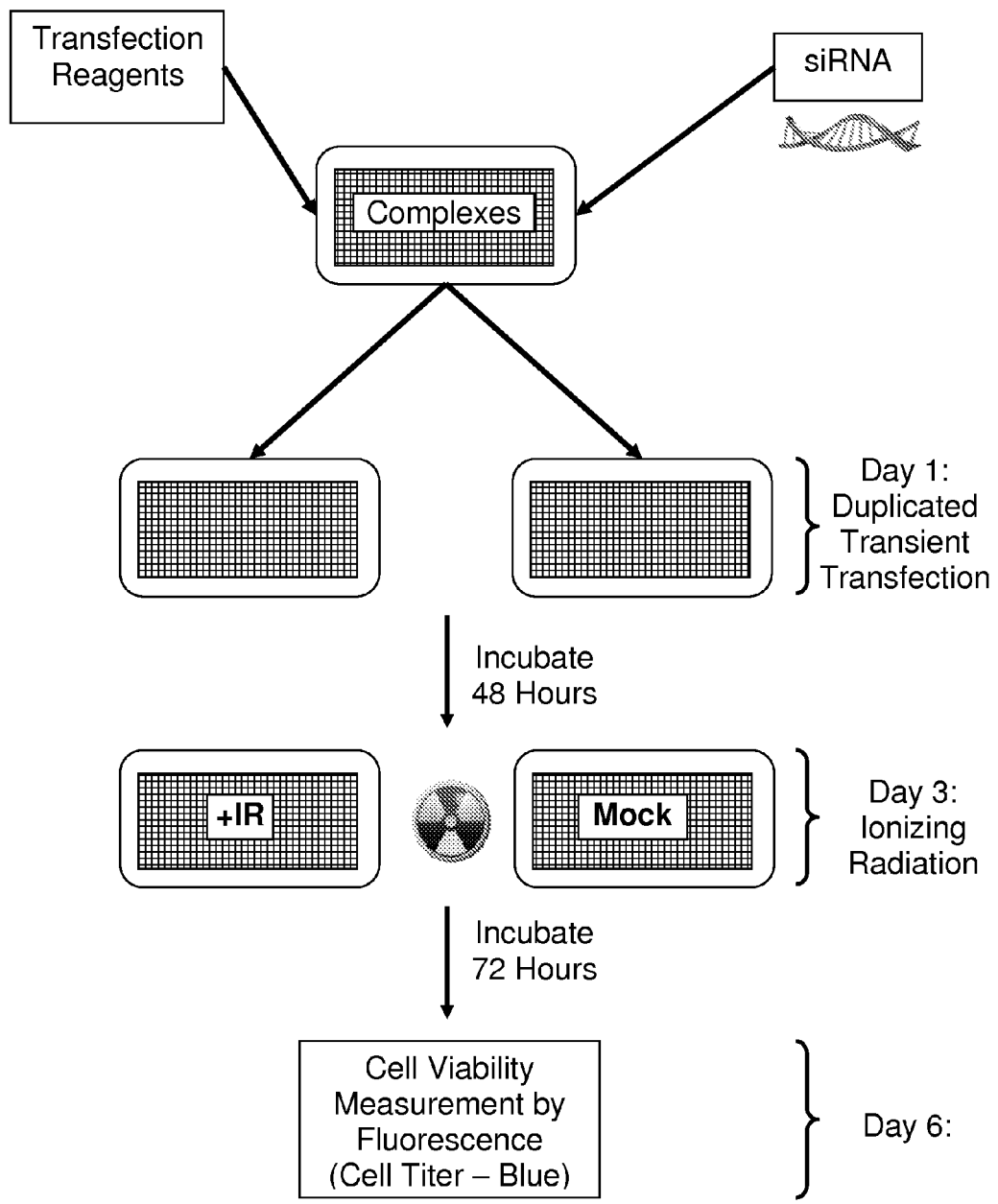
FIG. 1 Workflow diagram of siRNA library screening assay. Cells were reverse transfected on Day 1, exposed to either 25 Gy ionizing radiation or mock treatment on Day 3. Cell viability was measured on Day 6 by the CellTiter-Blue assay. For each compound tested, three individual screens were performed over three separate weeks.

Data presented are means±SD (n=3). *P<0.01 vs irradiated T98G cells in the absence of glyburide. (B) Chemical structure of glyburide.

FIG. 5 (A) Post-irradiation protective effect of glyburide in T98G cells. Glyburide was added to cell culture 30 min after irradiation exposure (25 Gy). (B) Radioprotective effect of glyburide on a range of γirradiation. Cells were incubated with 200 μM glyburide 1-h prior to γ-irradiation (5-25 Gy). (C) Radioprotective effect of glyburide in human glioblastoma U-87 MG cells and normal lung epithelial BEAS-2B cells. Cells were incubated with glyburide at indicated concentration 1-h prior to irradiation (10 Gy). (D) Radioprotective effect of glyburide in human primary astrocytes. Astrocytes were treated with glyburide (50 and 100 μM) 1-h prior to irradiation (25 Gy). Cell viability were determined with either flow cytometry (in A, B and C) or LDH release assay (in D). *, # P<0.01, 0.05 vs irradiated cells without glyburide treatment.

Figure 6:
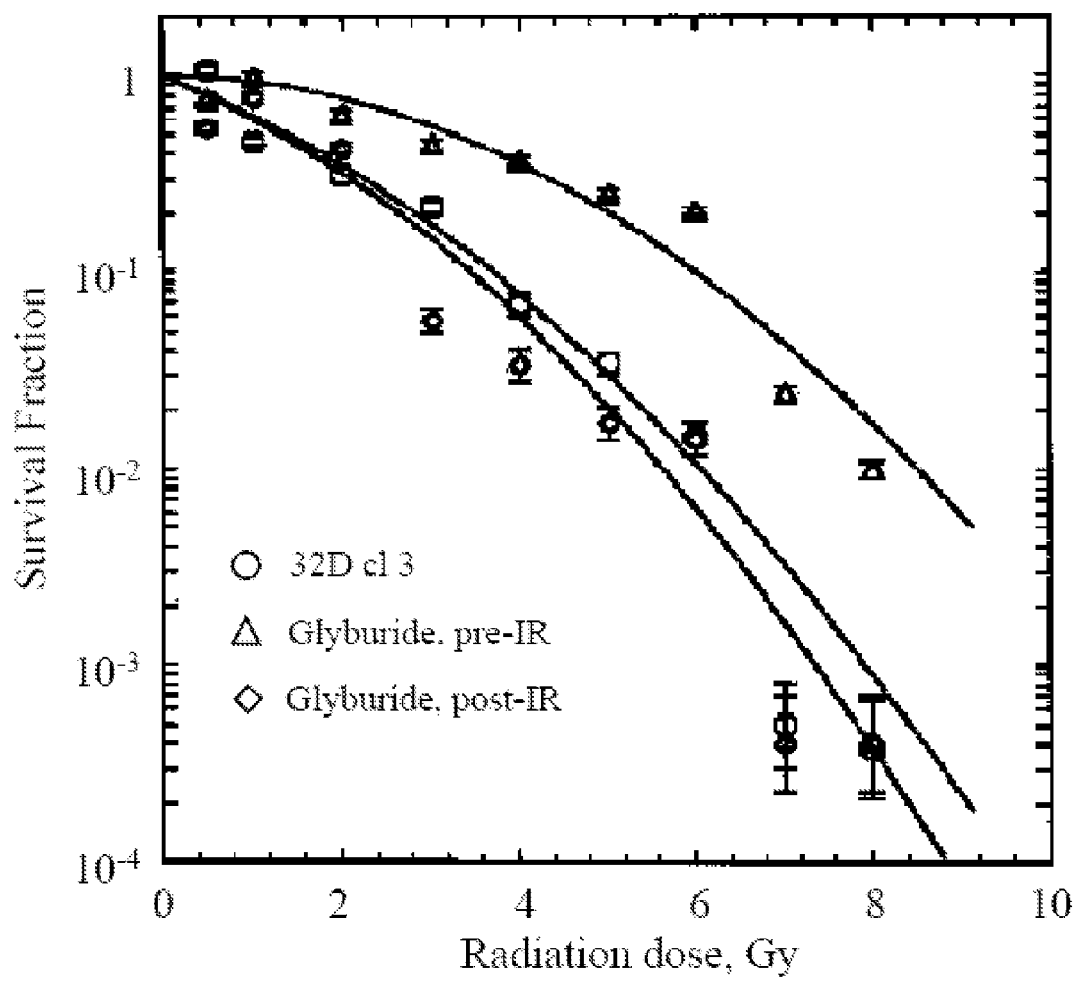

FIG. 6 is a graph showing survival of irradiated 32D cl 3 cells treated with glyburide before or after radiation exposure. Irradiation survival curves were performed in vitro by incubating 32D cl3 cells in 10 μM glyburide for 1 h before, or placing it in the methylcellulose that the cells were plated after irradiation. The surviving fraction was calculated as the plating efficiency of the samples relative to that of the control. The data was fitted to a linear quadratic model. Data presented are the mean±S.E. (n=3). Cells incubated in glyburide before irradiation were protected from irradiation as seen by an increased shoulder (n=34.9±0.5) on the survival curve compared to irradiated control cells or cells grown in glyburide (n=3.1±1.3 or 2.5±0.9) following irradiation (P<0.0018 or 0.0001, respectively). There was no significant change in the $D_0$ between the different conditions.

Figure 7:
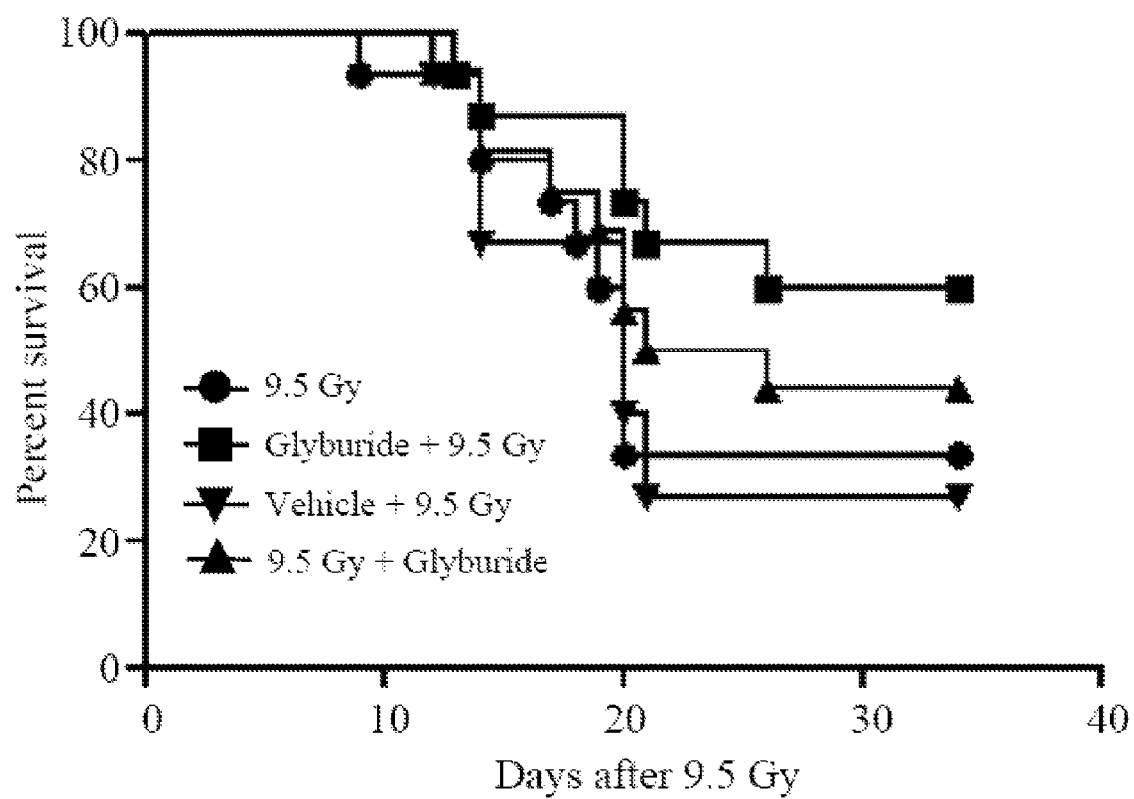

FIG. 7 is a graph showing radioprotective effect of glyburide on total body irradiation in mice. C57BL/6NHsd female mice were injected intraperitoneally with glyburide (5 mg/kg) 10-min before 9.5 Gy total body irradiation or 10-min after irradiation. Mice injected with glyburide before irradiation had a significantly increased survival compared to the control irradiated mice and mice injected with vehicle only (P=0.04). Injection of glyburide following irradiation had no significant increase in survival following irradiation.

DETAILED DESCRIPTION

The use of numerical values in the various ranges specified in this application, unless expressly indicated otherwise, are stated as approximations as though the minimum and maximum values within the stated ranges are both preceded by the word "about". In this manner, slight variations above and below the stated ranges can be used to achieve substantially the same results as values within the ranges. Also, unless indicated otherwise, the disclosure of these ranges is intended as a continuous range including every value between the minimum and maximum values. For definitions provided herein, those definitions also refer to word forms, cognates and grammatical variants of those words or phrases.

Methods are provided for protecting animals, such as mammals, including humans (collectively "subjects") against injury and/or death from exposure to ionizing radiation. The methods generally comprise administering to the subject an amount of a radioprotective agent to mitigate (lessen) damage, injury and/or death in the subject caused by the ionizing radiation.

The methods generally comprise administering an amount of a radioprotective agent to a subject effective to reduce, mitigate or (and/or) prevent injury or death from exposure of the subject to ionizing radiation. The radioprotective agent may be administered to a subject before, during or after exposure to ionizing radiation. As is shown in the examples, glyburide protected animals against exposure to ionizing radiation.

In a second, non-limiting embodiment, the methods comprise administering an amount of a radioprotective agent to a subject effective to mitigate apoptosis or injury or death from exposure of cells of the subject to an activator (e.g., causative agent) of oxidative stress-induced or DNA damage-induced apoptosis. The radioprotective agent may be administered to a subject before, during or after exposure to ionizing radiation or other activator of oxidative stress or DNA damage that can activate an apoptosis pathway in a cell. As is shown in the examples, glyburide effectively protects against cell death resulting from exposure of the cell to ionizing radiation. Cell death resulting from exposure to ionizing radiation primarily results from oxidative stress and DNA damage initiating an apoptosis pathway (See, e.g., Epperly, M W et al., Manganese Superoxide Dismutase (SOD2) Inhibits Radiation-Induced Apoptosis by Stabilization of the Mitochondrial Membrane Radiation Research 157 (2002) 568-77; Epperly, M W et al., Overexpression of the transgene for manganese superoxide dismutase (MnSOD) in 32D cl 3 cells prevents apoptosis induction by TNF-α, IL-3 withdrawal, and ionizing radiation, Experimental Hematology 31 (2003) 465-474; Epperly, M W et al., Mitochondrial Localization of Superoxide Dismutase is Required for Decreasing Radiation-Induced Cellular Damage Radiation Research 160 (2003) 568-578; Jiang, J et al., A Mitochondria-Targeted Nitroxide/Hemigramicidin S Conjugate Protects Mouse Embryonic Cells Against Gamma Irradiation Int. J. Radiation Oncology Biol. Phys., Vol. 70, No. 3 (2008) 816-825; and Epperly, M W et al., Ascorbate as a "Redox Sensor" and Protector Against Irradiation-Induced Oxidative Stress in 32d Cl 3 Hematopoietic Cells and Subclones Overexpressing Human Manganese Superoxide Dismutase, Int. J. Radiation Oncology Biol. Phys., Vol. 58, No. 3 (2004) 851-861). Administration of glyburide therefore mitigates steps in the activation of apoptosis resulting from exposure of cells to ionizing radiation or other events that cause oxidative stress and/or DNA strand breakage, such as exposure to chemical agents, such as cyclophosphamide or cis-platinum, as evidenced by reduced cell death as indicated in the experiments below.

In one non-limiting embodiment, the radioprotective agent is glyburide (also known as glibenclamide or 5-chloro-N-[2-[4-(cyclohexylcarbamoylsulfamoyl) phenyl]ethyl]-2-methoxy-benzamide, CAS No. 10238-21-8, PubChem Compound ID No. 3488). Glyburide is a hypoglycemic sulfonylurea used for the treatment of type II diabetes. It currently is broadly available in a number of dosage forms, for example and without limitation, as MICRONASE and as one of many generic forms. In the US, it is sold as oral tablets ranging in strength from 1.25 mg to 6 mg per tablet, including 1.25, 1.5, 2.5, 3, 4.5, 5 and 6 mg per tablet. Glyburide typically is administered in the range of from 1.25 mg to 20 mg daily to lower blood glucose. See, generally, U.S. Pat. Nos. 3,507,954, 4,060,634, 4,916,163, 6,830,760, for additional information regarding glyburide and uses therefor. A "hypoglycemic" or "hypoglycemic compound" is a compound that has the effect of lowering blood sugar in a subject when administered to the subject.

Any relevant end-point can be used to determine an amount of the radioprotective agent effective to protect an individual against radiation injury or death. The amounts useful as radioprotective agents in humans or other animals can be tested in animals and in accepted cell culture systems, such as described herein. Effective doses can be determined by reference to a therapeutic window between a minimum and maximum dose. The minimum dose is a dosage below which the radioprotective agent is not effective in mitigation of radiation injury or death. The maximum dosage is a dosage above which the drug causes undesirable side-effects, including undesirable hypoglycemia (in the case of glyburide or drugs with similar activity), death or other side-effects. By "effective," it is meant that death or injury due to radiation exposure is mitigated (reduced) to a clinically or statistically-relevant degree acceptable in the medical, pharmaceutical and/or veterinary arts. Given the serious nature of injury due to exposure to ionizing radiation, it may be better to administer a higher dosage of a drug than one would normally administer for other indications, such as is the case of the use glyburide as a radioprotective agent. Alternately, high dosages of glyburide or other hypoglycemic may be co-administered with glucose or other suitable sugars, either as part of the solid (e.g., tablet) dosage form or as an ingestable syrup or drink (e.g., soda or juice drink) to be co-administered with the drug. Glucose can be administered orally, parenterally or otherwise (e.g., intravenously), for example and without limitation in conjunction with post-treatment monitoring of blood glucose levels.

In any case, as used herein, any agent or agents used for reduction, prevention, or mitigation in a subject of injury caused by radiation exposure is administered in an amount effective to reduce, prevent, or mitigate such injury, namely in an amount and in a dosage regimen effective to prevent injury or to reduce the duration and/or severity of the injury resulting from radiation exposure. According to one non-limiting embodiment, an effective dose for glyburide may range from 0.1 or 1 mg/Kg to 20 mg/Kg, or from 4 to 6 mg/Kg including any increment or range therebetween, including 1 mg/Kg, 2 mg/Kg, 4 mg/Kg, 4.5 mg/Kg, 5 mg/Kg, 5.5 mg/Kg, 6 mg/Kg, 10 mg/Kg, 15 mg/Kg, and 20 mg/Kg. Target blood concentrations (including serum or plasma) for the compound may range, for example and without limitation, from 1 µM to 25 µM, or from 9 µM to 11 µM, including increments therebetween, including, without limitation, 1 µM, 2 µM, 5 µM, 9 µM, 9.5 µM, 10 µM, 10.5 µM, 11 µM, 15 µM, 20 µM and 25 µM. However, for each compound described herein, an effective dose or dose range is expected to vary from that of other compounds described herein for any number of reasons, including the molecular weight of the compound, bioavailability, specific activity, etc.

Compounds other than glyburide are expected to exhibit similar abilities to mitigate injury or death due to exposure to ionizing radiation. These compounds fall into two functionally-related classes. The first class is sulfonylurea hypoglycemics, which exhibit similar structure and function to glyburide, including, without limitation: acetohexamide (3-(4-acetylphenyl)sulfonyl-1-cyclohexylurea), tolazamide (1-(azepan-1-yl)-3-(4-methylphenyl)sulfonylurea), tolbutamide (1-butyl-3-(4-methylphenyl)sulfonylurea), chlorpropamide (1-(4-chlorophenyl)sulfonyl-3-propylurea), glipizide (N-[2-[4-(cyclohexylcarbamoylsulfamoyl)phenyl]ethyl]-5-methylpyrazine-2-carboxamide), gliclazide (1-(3,3a,4,5,6,6a-hexahydro-1H-cyclopenta[c]pyrrol-2-yl)-3-(4-methylphenyl)sulfonylurea), gliquidone (1-cyclohexyl-3-(p-beta-(4,4-dimethyl-2-methoxy-1,3-(2H,4H)-isoquinolinedione-2-yl)phenethyl)sulfonylurea), glyclopyramide (4-chloro-N-(pyrrolidin-1-ylcarbamoyl)benzenesulfonamide), and glimepiride (3-ethyl-4-methyl-N-[2-[4-[(4-methylcyclohexyl)carbamoylsulfamoyl]phenyl]ethyl]-2-oxo-5H-pyrrole-1-carboxamide)(see, e.g., Troy, D B, Editor, Remington: The Science and Practice of Pharmacy, $21^{st}$ Ed., Lippincott Williams & Wilkins (2005), pp. 1452-56).

The second class of compounds comprises compounds that are functionally related in that they are potassium channel inhibitors. Potassium channel inhibitors, include, without limitation, tetraethylammonium, 4-aminopyridine, glibenclamide tetraethylammonium agitoxin 2, charybdotoxin, apamin, and dendrotoxin. Other non-limiting examples of potassium channel inhibitors are disclosed in U.S. Pat. Nos. 6,566,380, 6,849,634, and 6,858,610; United States Patent Publication No 20080227778; International Patent Publication No. WO/2004/111057; and Grishin et al. (Structure and function of the potassium channel inhibitor from black scorpion venom Pure & App. Chem., Vol. 68, No. 11, pp. 2105-2109, 1996) describes non-limiting examples of potassium channel inhibitors.

The exact mechanisms of radioprotection action of glyburide remain unclear. Without any intention of being bound by this theory, one potential explanation is that, sulfonylurea hypoglycemics, including glyburide, act as ATP-sensitive potassium (KATP) channel (such as ABCC8) blockers and are widely used in diabetes treatment. These applications are based on the interactions of glyburide with sulfonylurea receptor 1 (SUR1)—the regulatory subunit of the pancreatic KATP channel—essential for triggering insulin secretion via membrane depolarization. It has also been reported that interactions of glyburide with SUR1 may play a role in the regulation of apoptosis (Hambrock A, de Oliveira Franz, C B Hiller S, Osswald H. Glibenclamide-induced apoptosis is specifically enhanced by expression of the sulfonylurea receptor isoform SUR1 but not by expression of SUR2B or the mutant SUR1(M1289T). J Pharmacol Exp Ther 2006; 316:1031-7. Wang L, Xu D, Dai W, Lu L. An Ultraviolet-activated K+ Channel Mediates apoptosis of Myeloblastic Leikemia cells. J Biol Chem 1999; 274:3678-85. Busija D W, Gaspar T, Domoki F, Katakam P V, Bari F. Mitochondrial-mediated suppression of ROS production upon exposure of neurons to lethal stress: Mitochondrial targeted preconditioning. Adv Drug Deliv Rev 2008). One possible mechanism is through the regulatory effects of glyburide on KATP channels, which participate in the regulation of apoptosis by controlling intracellular $Ca^{2+}$ level and affecting the mitochondrial permeability transition (MPT) pore. Indeed, several drugs, including glyburide, have been shown to act as regulators of this channel, hence affect execution of apoptotic program.

An amount effective to prevent apoptosis also can be determined by any useful end-point, such as by any appropriate/useful caspase assays, TUNEL and DNA fragmentation assays, cell permeability assays, Annexin V assays, protein cleavage assays, mitochondrial and ATP/ADP assays, etc.

The compounds described herein are useful in reducing, preventing or mitigating (to make less severe)) injury caused by radiation exposure. By radiation, in the context of this disclosure, it is meant types of radiation that result in the generation of free radicals, e.g., reactive oxygen species (ROS). The free radicals are produced, for example and without limitation, by direct action of the radiation, as a physiological response to the radiation and/or as a consequence of damage/injury caused by the radiation. In one embodiment, the radiation is ionizing radiation. Ionizing radiation consists of highly-energetic particles or waves that can detach (ionize) at least one electron from an atom or molecule. Examples of ionizing radiation are energetic beta particles, neutrons, and alpha particles. The ability of light waves (photons) to ionize an atom or molecule varies across the electromagnetic spectrum. X-rays and gamma rays can ionize almost any molecule or atom; far ultraviolet light can ionize many atoms and molecules; near ultraviolet and visible light are ionizing to very few molecules. Microwaves and radio waves typically are considered to be non-ionizing radiation, though damage caused by, e.g., microwaves may result in the production of free-radicals as part of the injury and/or physiological response to the injury.

The compounds are administered in an amount and dosage regimen to reduce, prevent, or mitigate the effects of exposure of a subject to radiation. The compounds may be administered in any manner that is effective to reduce, mitigateor prevent damage caused by the radiation. Examples of delivery routes include, without limitation: topical, for example, epicutaneous, inhalational, enema, ocular, otic and intranasal delivery; enteral, for example, orally, by gastric feeding tube and rectally; and parenteral, such as, intravenous, intraartedrial, intramuscular, inracardiac, subcutaneous, intraosseous, intradermal, intrathecal, intraperitoneal, transdermal, iontophoretic, transmucosal, epidural and intravitreal, with oral, intravenous, intramuscular and transdermal approaches being preferred in many instances. Given that glyburide is readily available as an oral dosage form, it may be preferable to administer that compound orally. Nevertheless, given that greater amounts of the compound than can be delivered orally might be needed, and that immediate effect might be needed, an intravenous, intramuscular or other parenteral delivery routes may be preferred. In one embodiment, the composition comprising the compound is administered by intramuscular injection using an automatic, triggerable injector (auto-injector), such as is used for administration of epinephrine, interferon beta-1a, morphine, atropine, pralidoxime chloride and diazepam.

The compounds may be compounded or otherwise manufactured into a suitable composition for use, such as a pharmaceutical dosage form or drug product in which the compound is an active ingredient. Compositions may comprise a pharmaceutically acceptable carrier, or excipient. An excipient is an inactive substance used as a carrier for the active ingredients of a medication. Although "inactive," excipients may facilitate and aid in increasing the delivery or bioavailability of an active ingredient in a drug product. Non-limiting examples of useful excipients include: antiadherents, binders, rheology modifiers, coatings, disintegrants, emulsifiers, oils, buffers, salts, acids, bases, fillers, diluents, solvents, flavors, colorants, glidants, lubricants, preservatives, antioxidants, sorbents, vitamins, sweeteners, etc., as are available in the pharmaceutical/compounding arts (see, Troy, D B, Editor, Remington: The Science and Practice of Pharmacy, $21^{st}$ Ed., Lippincott Williams & Wilkins (2005) for detailed descriptions of various dosage forms, methods of manufacture of such dosage forms and routes of administration of such dosage forms). In one embodiment, a sugar, such as glucose, is incorporated into the dosage form to counteract the hypoglycemic effects of a hypoglycemic agent included in the dosage form.

Useful dosage forms include: intravenous, intramuscular, or intraperitoneal solutions, oral tablets or liquids, topical ointments or creams and transdermal devices (e.g., patches). In one embodiment, the compound is a sterile solution comprising the active ingredient (drug, or compound), and a solvent, such as water, saline, lactated Ringer's solution, or phosphate-buffered saline (PBS), and optionally comprising glucose. Additional excipients, such as polyethylene glycol, emulsifiers, salts and buffers may be included in the solution. By "dose" it is meant an amount of a drug product administered to a subject at any given time, whether or not a single or unit dose, such as a single tablet, capsule, spray, puff, auto-injection, etc., or multiple unit doses are administered. An oral dosage form is a drug product that is suitable for administration orally, such as a tablet, capsule, caplet, syrup etc.

In one embodiment, the dosage form is a transdermal device, or "patch". The general structure of a transdermal patch is broadly known in the pharmaceutical arts. A typical patch includes, without limitation: a delivery reservoir for containing and delivering a drug product to a subject, an occlusive backing to which the reservoir is attached on a proximal side (toward the intended subject's skin) of the backing and extending beyond, typically completely surrounding the reservoir, and an adhesive on the proximal side of the backing, surrounding the reservoir, typically completely, for adhering the patch to the skin of a patient. The reservoir typically comprises a matrix formed from a non-woven (e.g., a gauze) or a hydrogel, such as a polyvinylpyrrolidone (PVP) or polyvinyl acetate (PVA), as are broadly known. The reservoir typically comprises the active ingredient absorbed into or adsorbed onto the reservoir matrix, and skin permeation enhancers. The choice of permeation enhancers typically depends on empirical studies.

Doses of the compound may be administered prior to, during or after exposure to radiation. Timing of the dosing, and dosage regimens will depend on the timing of peak blood levels of the compound or bioavailability of the compound from the dosage form. For instance, when the composition is delivered orally, it typically would have to be administered further in advance than an injectable dosage form. Half life of the compound in the subject's blood, along with the estimated duration of exposure to the radiation and/or duration needed for protection against damage and/or apoptosis, would determine if repeated doses are necessary. For hypoglycemics, it may be desirable to-administer a sugar (e.g., glucose), either as part of the dosage form, or at a time period effective to counter the blood sugar-lowering effects of the compound.

As is illustrated below, also provided herein is a method of identifying a composition having radioprotective activity. The method comprises: transforming cells with an interfering RNA (that is by RNA interference or RNAi), such as, without limitation, siRNA, microRNA (miRNA), dsRNA cleavage or RNA-induced silencing complex (RISC) methods, or otherwise inhibiting expression of a gene—the expression of which can be inhibited by an active agent (that is the gene is part of a druggable genome). The method further comprises culturing the transformed cells in a first cell culture and non-transformed cells in a second cell culture; irradiating the transformed cells and non-transformed cells with an amount of ionizing radiation that is lethal to the cells; and determining if inhibition of expression of the gene resulted in a radioprotective effect by determining if more cells survived in the first cell culture as compared to the second cell culture, thereby indicating that the active agent is radioprotective.

EXAMPLES

This study was designed to test the hypothesis that well-characterized drugs contain previously unknown radioprotective action using a synthetic protection assay in which siRNA that were per se nontoxic were protective against a cytotoxic dose of ionizing irradiation. We used an siRNA library comprising 16,560 unique siRNA sequences targeting 5,520 genes (Table 1) that encode gene transcripts considered actual or potential drug targets or disease modifying. Surprisingly, we identified a commonly used hypoglycemic agent that protects against lethal doses of irradiation. These results illustrate the power of a combined approach of high-throughput siRNA screening and conventional cell-based assay leading to the discovery of radioprotectants.

Methods

Reagents.

DharmaFECT 2 transfection reagent and 5× siRNA resuspension buffer were from Dharmacon (Lafayette, Colo.). CellTiter-Blue Cell Viability Assay was from Promega (Madison, Wis.). The 384-well tissue-culture treated microtiter plates were from Greiner Bio-One (GmbH, Frickenhausen, Germany). OptiMEM, MEM, and FBS were from Invitrogen (Carlsbad, Calif.). The Silencer Druggable Genome siRNA Library (Version 1.1) was from Ambion (Austin, Tex.). Annexin V kit was from Biovision (Mountain View, Calif.). Lactate dehydrogenase (LDH) viability kit was from Sigma (St. Louis, Mass.).

Cell Culture.

Human glioblastoma T98G and U-87 MG cells (American Type Culture Collection, Manassas, Va.), were maintained in MEM medium supplemented with 2 mM glutamine, 10% FBS and penicillin-streptomycin. Human primary astrocytes were purchase from ScienCell (Carlsbad, Calif.) and maintained according to the manufacturer's instruction. Normal human lung epithelial BEAS-2B cells were from American Type Culture Collection and cultured in a serum-free bronchial epithelial growth medium (Lonza, Walkersville, Md.). The 32D cl 3 mouse hematopoietic progenitor cell line, dependent for growth upon interleukin 3 (IL-3), has been described previously (Epperly, M. W., Guo, H., Gretton, J. E. & Greenberger, J. S. Bone marrow origin of myofibroblasts in irradiation pulmonary fibrosis. *Am. J. Respir. Cell Mol. Biol.* 29, 213-224 (2003)). 32D cl 3 cells were passaged in fresh RMPI 1640 medium containing 10% FBS, 1% glutamine, penicillin-streptomycin, and 15% WEHI3 conditioned medium as a source of IL-3.

High Throughput siRNAs Delivery by Reverse Transfection.

Human glioblastoma T98G cells were reverse transfected (Amarzguioui, M. Improved siRNA-mediated silencing in refractory adherent cell lines by detachment and transfection in suspension. *Biotechniques* 36: 766-770 (2004)) with the siRNA library in 384-well plate at a final concentration of 20 nM/target in a one-gene, one-well format. The siRNA complexes were prepared by mixing DharmaFECT 2 transfection reagent with a pool of three unique siRNA duplexes (each designed against a different region of the target transcript) per well, in OptiMEM serum free medium. T98G cell suspension in culture medium was added directly onto the siRNA complexes. The siRNA containing medium was replaced with fresh complete culture medium 5 h later. Cells were incubated for 48 h to allow for gene silencing (Tyner, T. W. et al. RNAi screening of the tyrosine kinome identifies therapeutic targets in acute myeloid leukemia. *Blood* 11, 2238-2245 (2008)) before γ-irradiation (25 Gy) or mock treatment. Cell viability was measured with the CellTiter-Blue cell viability assay according to manufacturer's protocol 72-h post irradiation incubation.

Threshold for Selecting Primary Radioprotective siRNA.

The irradiation siRNA screen was performed three times over three separate weeks. A candidate radioprotective siRNA was identified if the siRNA protected T98G cells ≥15% from irradiation-mediated cell death in each of three independent screens.

Validation of Target with a Cell-Based Assay.

Cells were cultured in fresh medium prior to irradiation and were γ-irradiated with a Shepherd model 143-45A irradiator (J. L. Shepherd & Associates, CA) at a dose rate of 4 Gy/min. Cells were incubated with drugs at the indicated concentrations 1 h before or 30 min after irradiation. Cell viability was determined using phosphatidylserine (PS) externalization/propidium iodide (PI) permeabilization assay or LDH Assay after 72 h post-irradiation incubation.

PS Externalization/PI Permeabilization Assay.

After 72 h post-irradiation incubation, attached cells were harvested by trypsinization and pooled with detached cells from supernatant. Harvested cells were then stained with annexin-V-FITC and PI for 5 min in the dark prior to flow cytometry analysis (FACscan, Becton-Dickinson, Rutherford, N.J.). Cell debris was gated out by forward and side scatter under the same conditions, and a minimum of 10,000 gated cells were acquired. Percentages of annexin-V-positive cells were calculated by combining annexin V+/PI− (early apoptotic) and annexin V+/PI+ (late apoptotic or necrotic) cells.

LDH Assay.

For human primary astrocytes, cell viability was determined by assaying the medium from each sample for LDH activity according to the manufacturer's instructions (Sigma). The enzyme activity from the culture medium and floating cells were used as an index of cell death. To determine total LDH activity, the adherent cells were lysed in 0.5% Triton X-100 and assayed for LDH activity, this cell-associated LDH activity was then added to the LDH activity in the removed culture medium. The amount of LDH present in the medium was calculated as a percentage of the total, which was used to calculate the percent cell death in the corresponding samples.

In Vitro Irradiation Survival Curves.

Murine hematopoietic progenitor cells 32D cl 3 cells were incubated in the presence of 10 µM glyburide 1 hr before or after irradiation by adding glyburide to the methycellulose in which the cells were incubated following irradiation. The cells were irradiated with doses ranging from 0 to 8 Gy. The 32D cl 3 cells were plated in methycellulose, incubated at 37° C. for one week at which time colonies of greater than 50 cells were counted (Epperly, M. W. et al. Mitochondrial localization of superoxide dismutase is required for decreasing radiation induced cell damage. *Radiat. Res.* 160, 568-578 (2003) and Epperly, M. W. et al. Ethyl pyruvate, a potentially effective total body irradiation damage mitigator. *Radiat. Res.* 168, 552-559 (2007)). The data were analyzed using linear quadratic and single-hit, multi-target models (Id.).

In Vivo Irradiation Survival Curves.

The ability of glyburide to protect the hematopoietic system from irradiation was tested using irradiation survival curves as previously described (Epperly, M. W. et al. Overexpression of MnSOD transgene product protects cryopreserved bone marrow hematopoietic progenitor cells from ionizing irradiation. *Radiat. Res.* 168, 560-566 (2007)). Glyburide was dissolved in a 50:50 solution of cremophor EL and ethanol which was then diluted 1:4 in water. Female C57BL/6NHsd mice (15 per group) were injected intraperitoneally with glyburide (5 mg/kg) either 10 min before or 10 min after 9.5 Gy total body irradiation. Other groups of mice were control mice, or vehicle only irradiated mice. Mice were followed for the development of the irradiation-induced hematopoietic syndrome as demonstrated by a loss of weight and activity as well as decreased activity at which time they were sacrificed.

Statistics.

All data were expressed as means±SD of at least three independent experiments. Data from the in vitro irradiation survival curves were analyzed by a student's t test while the survival data were analyzed by a log rank test ((Epperly, M. W. et al. *Radiat. Res.* 160, 568-578 (2003) and Epperly, M. W.

et al. *Radiat. Res.* 168, 552-559 (2007))). Statistical comparisons between different groups were performed by student's t-test. P<0.05 was considered significant.

Results

An Automated Druggable Genome Radioprotective siRNA Library Screen

We have used a high-density 384-well plate format and large-scale siRNA screen to rapidly and robustly identify genes that modulate human glioblastoma T98G cell sensitivity to γ-radiation (25 Gy). Employment of T98G cells are an attractive model because they are known to be relatively resistant for irradiation (Rübel, A. et al. The membrane targeted apoptosis modulators erucylphosphocholine and erucylphosphohomocholine increase the radiation response of human glioblastoma cell lines in vitro. *Radiat. Oncol.* 1, 6 (2006)), providing the advantage of screening to identify both radiosensitizing and radiation resistance-inducing genes.

Figure 2:
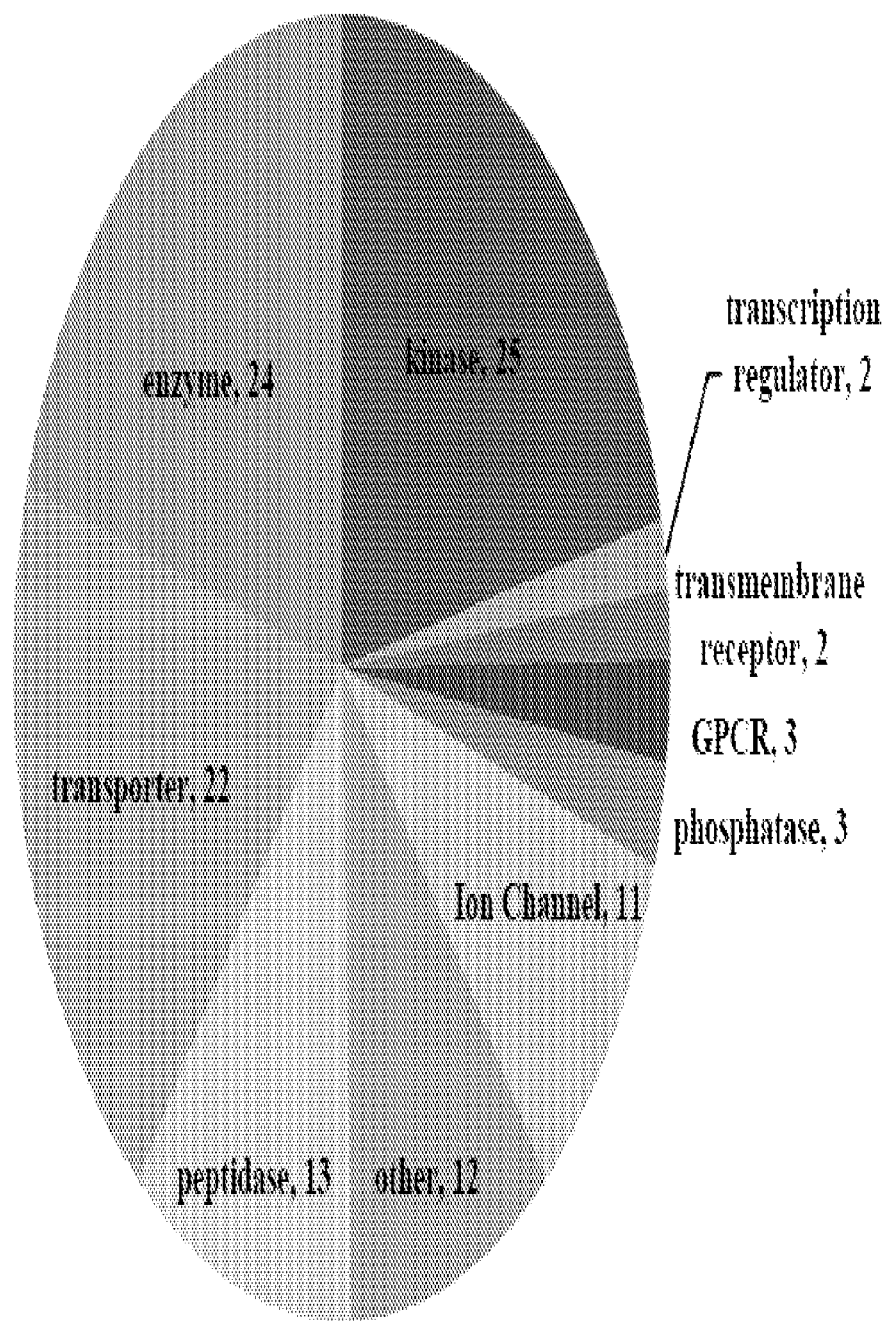
FIG. 2 Functional categories of the 116 primary radioprotective siRNA. The siRNA library screens were performed in triplicate, identifying siRNAs that reproducibly protected cells from a 25 Gy dose of γ irradiation.
Figures 3A, 3B:
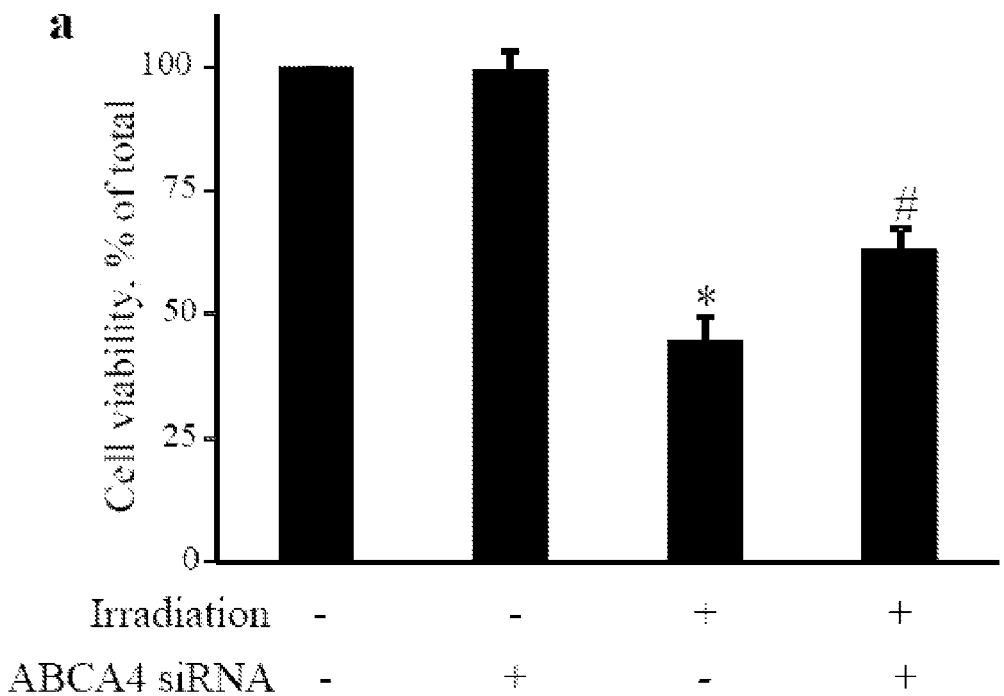
(FIG. 3A) Cell viability was measured with CellTiter-Blue after 72 hours post-irradiation incubation, and is shown as a percentage of the viability of cells transfected with control siRNA duplexes. Data are plotted as the means±SD of three different experiments. *$P<0.01$ vs siRNA transfected cells without irradiation, # $P<0.05$ vs irradiated cells without siRNA transfection.
(FIG. 3B) Sequences for the three unique siRNA duplexes targeting ABCA4 (Duplex #1, SEQ ID NOS: 1 and 2; Duplex #2, SEQ ID NOS: 3 and 4; and Duplex #3, SEQ ID NOS: 5 and 6).

The six-day workflow of the siRNA screening is illustrated in FIG. 1. siRNA molecules (final concentration, 20 nM) were added to the wells, targeting one gene per well, plus in-plate scrambled siRNA control wells on every plate. For each of the 5,520 genes (Table 1), we pooled three unique siRNA duplexes to reduce the cost and improve throughput. Transfection complexes were prepared using automated liquid handling instruments, and after 15-20 min, transfection complexes were divided among two new 384-well plates followed by the addition of T98G cells in suspension. Plate pairs were incubated for 48 h before γ-irradiation (25 Gy) or mock treatment. Seventy-two hours later, cell viability was measured by the CellTiter-Blue assay. Based on reproducible data from three independent siRNA screens with γ-radiation with T98G cells, we identified 116 genes that, when silenced, protect cells (Table 2). Among these genes were transporters, kinases, transcription regulators, transmembrane receptors, G-protein coupled receptors, phosphatases, ion channel and peptidases (Table 2 and FIG. 2). FIG. 3 illustrates an example of protective siRNA, which silenced ATP-binding cassette, subfamily A (ABC1), member 4 (ABCA4). Silencing of ABCA4 with siRNA duplexes exerted no obvious effect on cell viability in T98G cell while a 25 Gy dose of γ-irradiation inhibited cell viability by 53%. Silencing of ABCA4 prior to radiation reproducibly protected cells by 31%.

TABLE 1

List of gene categories in Silencer Druggable Genome siRNA Library v.1.1

| Subset | Genes |
| --- | --- |
| GPCR subset | 431 |
| Transferase subset | 345 |
| Receptor subset | 295 |
| Other transporter subset | 257 |
| GO kinase subset | 253 |
| Dehydrogenase subset | 186 |
| Hydrolase Related subset | 173 |
| Transferase Related subset | 164 |
| Metallo Protease subset | 157 |
| Other Phosphatase subset | 151 |
| Serine Protease subset | 141 |
| Ras G Protein subset | 101 |
| Other G protein subset | 96 |
| Cysteine Protease subset | 87 |
| TK Kinase subset | 84 |
| Voltage Gated Potassium Channel subset | 76 |
| Silence ®Other kinase subset | 72 |
| CAMK Kinase subset | 68 |
| Dehydrogenase Related subset | 67 |
| Reductase subset | 65 |
| Other Ion Channels subset | 63 |
| Miscellaneous subset | 62 |
| Carrier Related subset | 59 |
| AGC Kinase subset | 58 |
| CMGC kinase subset | 57 |
| Other Protease subset | 57 |
| Oxidase subset | 56 |
| Nuclear Hormone Receptor subset | 53 |
| Cytochrome P450 subset | 52 |
| ATP Binding Cassette (ABC) Transporter subset | 50 |
| Isomerase Related subset | 46 |
| Ubiquitin subset | 46 |
| Receptor Related subset | 45 |
| Hydroxylase subset | 43 |
| Kinesin subset | 42 |
| Lipase Related subset | 42 |
| STE kinase subset | 42 |
| TKL Kinase subset | 41 |
| Tyrosine Phosphatase subset | 41 |
| Atypical Kinase subset | 40 |
| Isomerase subset | 40 |
| Synthetase subset | 40 |
| Hydrogen Transporter subset | 39 |
| Caspase subset | 38 |
| Phosphodiesterase Library | 38 |
| Myosin subset | 37 |
| Proteinase subset | 34 |
| Peptidase subset | 33 |
| Solute Carrier subset | 33 |
| Glutamate Neurotransmitter subset | 32 |
| ATPase subset | 31 |
| Cyclin subset | 31 |
| Lipase subset | 28 |
| Voltage Gated Calcium Channel subset | 28 |
| Esterase subset | 27 |
| Carboxylase Related subset | 25 |
| Other ligand Ion Channels subset | 25 |
| Oxygenase subset | 25 |
| Unassigned siRNA | 25 |
| Anion Channels subset | 23 |
| Tubulin subset | 23 |
| Kinase Related subset | 22 |
| Carboxylase subset | 21 |
| GABA Neurotransmitter subset | 20 |
| Synthase subset | 20 |
| Adhesion Molecule subset | 19 |
| ATP Carbohydrate Transporter subset | 19 |
| Dynein subset | 19 |
| Peptidase Inhibitor subset | 19 |
| Acetylcholine Neurotransmitter subset | 18 |
| Esterase Related subset | 18 |
| Oxidoreductase subset | 18 |
| Reductase Related subset | 18 |
| Integrin | 17 |
| Ligase | 17 |
| Lyase and Related subset | 17 |
| Oxidase Related subset | 17 |
| Aspartic Protease subset | 16 |
| BCL2 and Related subset | 16 |
| Polymerase subset | 16 |
| Protein Exchange G Protein Subset | 16 |
| Amino Acid Transporter subset | 15 |
| Heterotrimeric G Protein subset | 15 |
| Ribonuclease subset | 15 |
| Dehydratase subset | 14 |
| Voltage gated - sodium subset | 14 |
| Other Neurotransmitter subset | 13 |
| Deaminase subset | 12 |
| CK kinase subset | 11 |
| ATPase Related subset | 10 |
| Hydroxylase Related subset | 10 |
| Guanylate Cyclase subset | 9 |
| Adenylate Cyclase subset | 8 |
| Cyclic Nucleotide Gated Ion Channel subset | 8 |
| Dehydratase Related subset | 8 |
| Helicase subset | 7 |
| Glucosidase subset | 7 |
| Oxygenase Related subset | 7 |

TABLE 1-continued

List of gene categories in Silencer Druggable Genome siRNA Library v.1.1

| Subset | Genes |
| --- | --- |
| Protease Inhibitor subset | 7 |
| Deacetylase subset | 6 |
| Integrin Related subset | 6 |
| Synthase Related subset | 6 |
| Synthetase Related subset | 6 |
| Cytochrome P450 Related subset | 5 |
| Endonuclease subset | 5 |
| Non Solute Carrier subset | 5 |
| Other Cyclase subset | 4 |
| RNA binding subset | 3 |
| Exonuclease subset | 2 |

TABLE 2

| Symbol | Gene Name |
| --- | --- |
| AADAT | aminoadipate aminotransferase |
| ABCA4 | ATP-binding cassette, subfamily A, member 4 |
| ABCA8 | ATP-binding cassette, subfamily A, member 8 |
| ABCC8 | ATP-binding cassette, subfamily C (CFTR/MRP), member 8 |
| ACCN2 | amiloride-sensitive cation channel 2, neuronal |
| ACOXL | acyl-Coenzyme A oxidase-like |
| ADAM10 | ADAM metallopeptidase domain 10 |
| ADAMTS17 | ADAM metallopeptidase with thrombospondin type 1 motif, 17 |
| ALDH1A3 | aldehyde dehydrogenase 1 family, member A3 |
| ALDH1B1 | aldehyde dehydrogenase 1 family, member B1 |
| ALDH4A1 | aldehyde dehydrogenase 4 family, member A1 |
| ARHGEF6 | Rac/Cdc42 guanine nucleotide exchange factor (GEF) 6 |
| ATP8A2 | ATPase, aminophospholipid transporter-like, class I, type 8A, 2 |
| CACNA1B | calcium channel, voltage-dependent, N type, alpha 1B subunit |
| CAMK2B | calcium/calmodulin-dependent protein kinase (CaM kinase) II beta |
| CAPN13 | calpain 13 |
| CAPN2 | calpain 2, (m/II) large subunit |
| CAPNS2 | calpain, small subunit 2 |
| CARD9 | caspase recruitment domain family, member 9 |
| CATSPER2 | cation channel, sperm associated 2 |
| CHRNA1 | cholinergic receptor, nicotinic, alpha 1(muscle) |
| CHRNB2 | cholinergic receptor, nicotinic, beta 2(neuronal) |
| COX8A | cytochrome c oxidase subunit 8A (ubiquitous) |
| CSNK1G2 | casein kinase 1, gamma 2 |
| CTSA | cathepsin A |
| CYP3A5 | cytochrome P450, family 3, subfamily A, polypeptide 5 |
| DGKQ | diacylglycerol kinase, theta 110 kDa |
| DMPK | dystrophia myotonica-protein kinase |
| DUSP22 | dual specificity phosphatases 22 |
| DYPK1B | dual-specificity tyrosine-(Y)-phosphorylation regulated kinase 1B |
| ECE1 | endothelin converting enzyme 1 |
| ENPP3 | ectonucleotide pyrophosphatase/phosphodiesterase 3 |
| EPHA1 | EPH receptor A1 |
| EPHB2 | EPH receptor B2 |
| FOLR1 | Folate receptor 1 (adult) |
| GABRD | gamma-aminobutyric acid (GABA) A receptor, delta |
| GALK2 | galactokinase 2 |
| GCDH | glutaryl-Coenzyme A dehydrogenase |
| GRM8 | glutamate receptor, metabotropic 8 |
| H6PD | hexose-6-phosphate dehydrogenase (glucose 1-dehydrogenase) |
| HARS2 | hisdyl-tRNA synthetase 2, mitochondrial (putative) |
| IBSP | integrin-binding sialoprotein (bone sialoprotein, bone sialoprotein II) |
| KCNE2 | potassium voltage-gated channel, Isk-related family, member 2 |
| KCNG1 | potassium voltage-gated channel, subfamily G, member 1 |
| KCNK4 | potassium voltage-gated channel, subfamily G, member 1 |
| KCNK9 | Potassium channel, subfamily K, member 9 |
| KLK5 | kallikrein-related peptidase 5 |

TABLE 2-continued

| Symbol | Gene Name |
| --- | --- |
| LMLN | leishmanolysin-like (metallopeptidase M8 family) |
| MAPKAPK2 | mitogen-activated protein kinase-activated protein kinase 2 |
| MC2R | melanocortin 2 receptor (adrenocorticotropic hormone) |
| MED16 | mediator complex subunit 16 |
| MLKL | mixed lineage kinase domain-like |
| MMP27 | matrix metallopeptidase 27 |
| MMP3 | matrix metallopeptidase 3 (stromelysin 1, progelatinase) |
| MMP9 | matrix metallopeptidase 9 |
| MST1R | macrophage stimulating 1 receptor (c-met-related tyrosine kinase) |
| MTHFD2 | methylenetetrahydrofolate dehydrogenase (NADP+ dependent) 2 |
| NME4 | non-metastatic cells 4, protein expressed in |
| NME6 | non-metastatic cells 6, protein expressed in |
| OAS3 | 2'-5'-oligoadenylate synthetase 3, 100 kDa |
| OFD1 | oral-facial-digital syndrome 1 |
| PAK1 | p21/Cdc42/Rac1-activated kinase 1(STE20 homolog, yeast) |
| PAK4 | p21(CDKN1A)-activated kinase 4 |
| PCCB | propionyl Coenzyme A carboxylase, beta polypeptide |
| PDE11A | phosphodiesterase 11A |
| PDE2A | phosphodiesterase 2A, cGMP-stimulated |
| PDE4B | phosphodiesterase 4B, cAMP-specific |
| PDE4D | Phosphodiesterase 4D, cAMP-specific |
| PDE6C | Phosphodiesterase 6C, cGMP-specific, cone, alpha prime |
| PIGH | phosphatidylinositol glycan anchor biosynthesis, class H |
| PIP5K1B | phosphatidylinositol-4-phosphate 5-kinase, type I, beta |
| PKIA | protein kinase (cAMP-dependent, catalytic) inhibitor alpha |
| PRPS1L1 | phosphoribosyl pyrophosphate synthetase 1-like 1 |
| PRSS1 | protease, serine, 1 (trypsin 1) |
| PTPN9 | protein tyrosine phosphatase, non-receptor type 9 |
| PTPRA | protein tyrosine phosphatase, receptor type, A |
| REV1 | REV1 homolog (S. cerevisiae) |
| RFPL3 | ret finger protein-like 3 |
| ROR2 | receptor tyrosine kinase-like orphan receptor 2 |
| SKP2 | S-phase kinase-associated protein 2 (p45) |
| SLC10A1 | solute carrier family 10, member 1 |
| SLC15A1 | solute carrier family 15, (oligopeptide transporter), member 1 |
| SLC16A3 | solute carrier family 16, member 3 |
| SLC17A5 | solute carrier family 17 (anion/sugar transporter), member 5 |
| SLC18A2 | solute carrier family 18 (vesicular monoamine), member 2 |
| SLC19A1 | solute carrier family 19 (folate transporter), member 1 |
| SLC1A6 | solute carrier family 1, member 6 |
| SLC25A22 | solute carrier family 25, member 22 |
| SLC27A3 | solute carrier family 27 (fatty acid transporter), member 3 |
| SLC44A5 | solute carrier family 44, member 5 |
| SLC4A9 | solute carrier family 4, member 9 |
| SLC6A1 | solute carrier family 6, member 1 |
| SLC6A2 | solute carrier family 6, member 2 |
| SLC6A3 | solute carrier family 6, member 3 |
| SLCO4C1 | solute carrier organic anion transporter family, member 4C1 |
| SRM | spermidine synthase |
| STK24 | serine/threonine kinase 24 (STE20 homolog, yeast) |
| STK39 | serine threonine kinase 39 (STE20/SPS1 homolog, yeast) |
| STX11 | syntaxin 11 |
| STX4 | syntaxin 4 |
| TAP1 | transporter 1, ATP-binding cassette, subfamily B (MDR/TAP) |
| TGFB1/1 | transforming growth factor beta 1 induced transcript 1 |
| TLL2 | tolloid-like 2 |
| TMEM 11 | transmembrane protein 11 |
| TMPRSS9 | transmembrane protease, serine 9 |
| TRIB3 | tribbles homolog 3 (Drosophila) |
| TRMT1 | TRM1 tRNA methyltransferase 1 homolog (S. cerevisiae) |
| TRPC1 | transient receptor potential cation channel, subfamily C, memb 1 |
| TRPC3 | transient receptor potential cation channel, subfamily C, memb 3 |
| TRPC4 | transient receptor potential cation channel, subfamily C, memb 4 |
| TSSK6 | testis-specific serine kinase 6 |
| TTL | tubulin tyrosine ligase |
| UCK1 | uridine - cytidine kinase 1 |
| VAV3 | vav 3 guanine nucleotide exchange factor |
| WDR31 | WD repeat domain 31 |
| WNK1 | WNK lysine deficient protein kinase 1 |

Target Validation Using Small Molecule Inhibitors

Figure 4A:
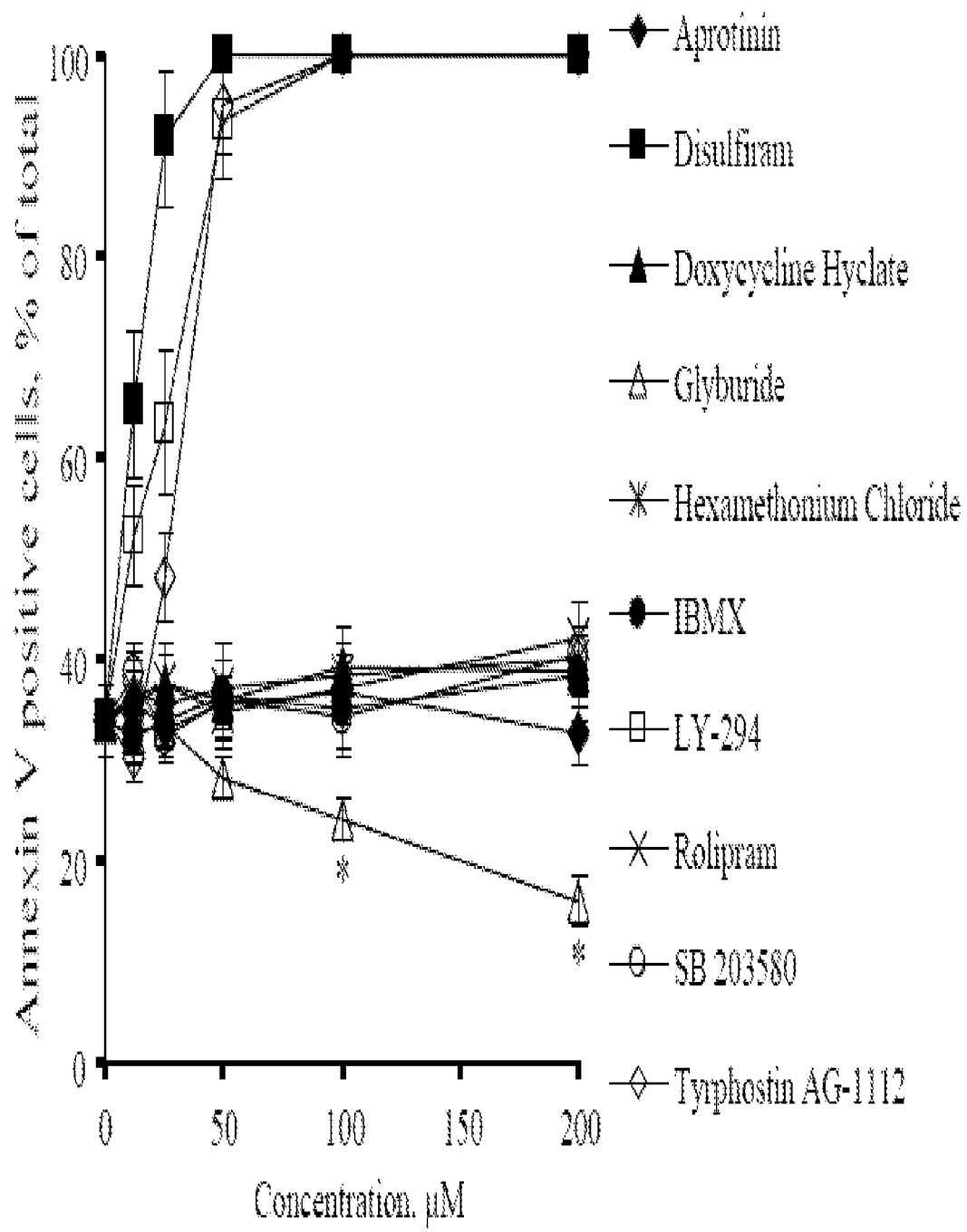
FIG. 4 Target validation using small molecular inhibitors in human glioblastoma T98G cells. (A) Effect of inhibitors on γ-irradiation induced cell death in T98G cells. Cells were seeded in 35 mm dishes at a density of $10^5$/dish and allowed to attach overnight. Cells were incubated with inhibitors at indicated concentration 1-h prior to γ-irradiation (25 Gy). After 72 hours post-irradiation incubation, cell death was assessed by flow cytometry using an annexin-V-FITC/PI kit.
Figure 4B:
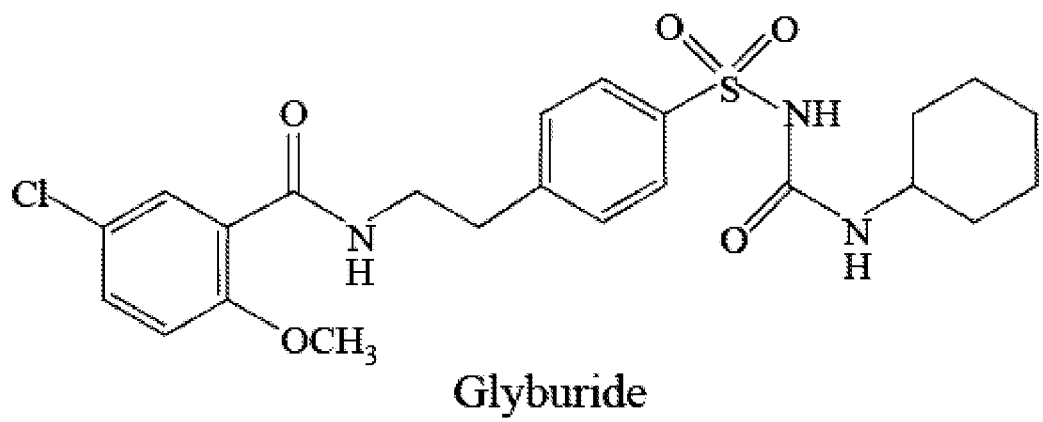
Figure 5A:
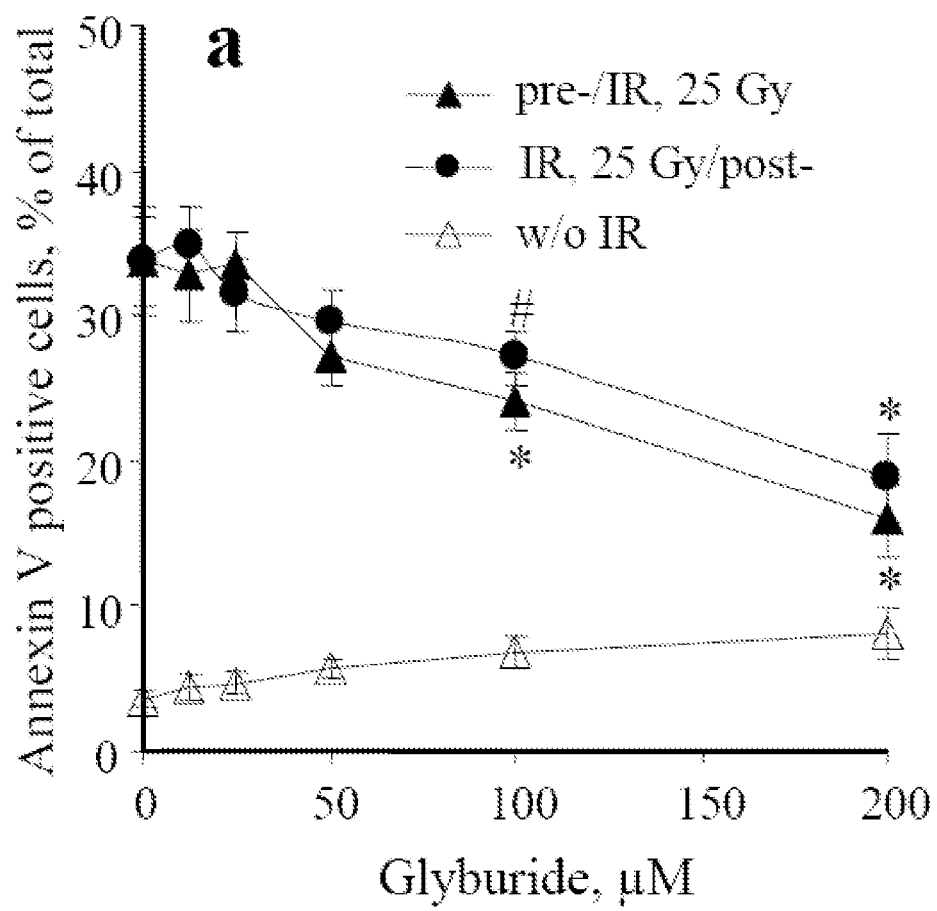
Figure 5B:
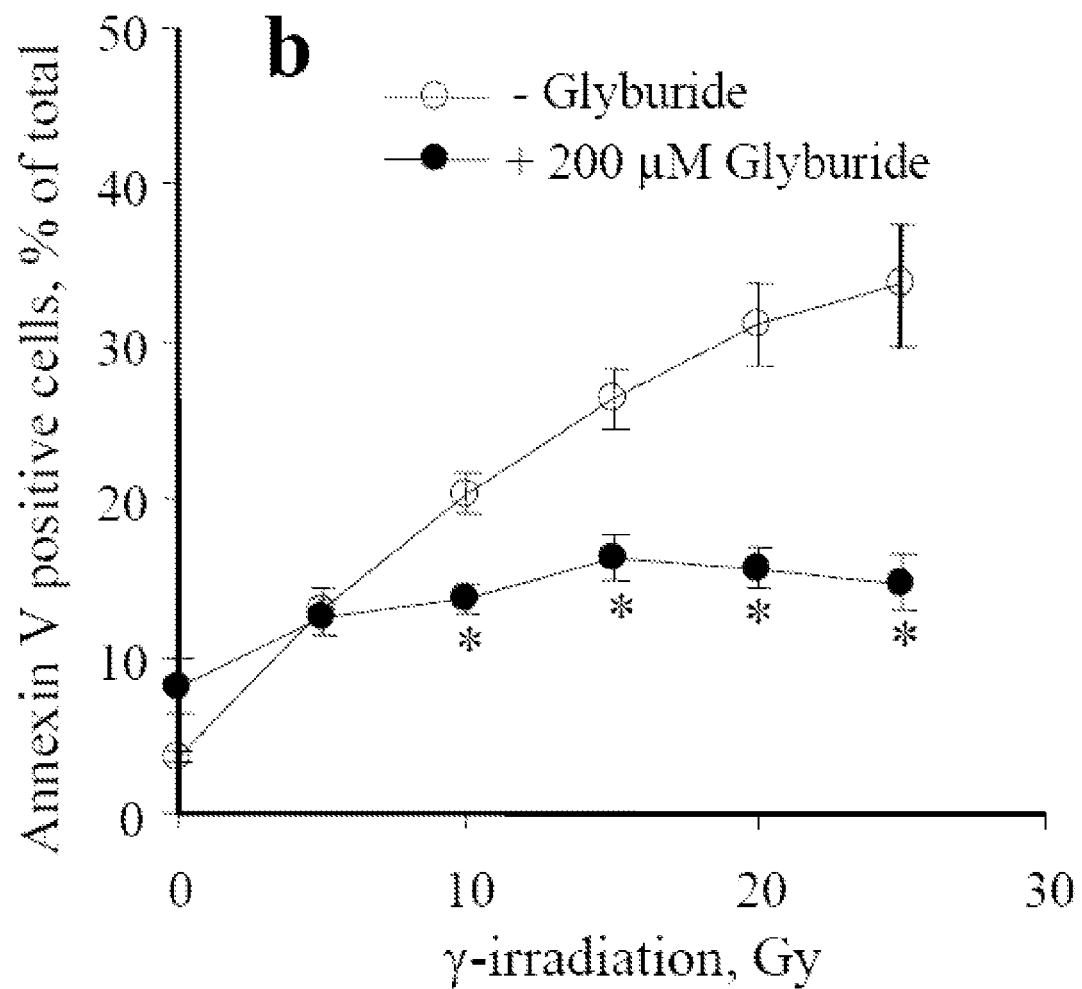

In the present study, we selected 10 chemicals that targeted 13 candidate siRNA gene transcripts for further study (Table 3). The radioprotective effects of the compounds were tested in T98G cells, which were initially used in the siRNA screen. The irradiation-induced cell death was determined by phosphatidylserine (PS) externalization and propidium iodide (PI) permeability using flow cytometry and ~30% of cells displayed externalized PS and/or increased membrane permeability 72-h post γ-irradiation (25 Gy) incubation. Among the 10 compounds tested, glyburide (FIG. 4B), a second-generation sulfonylurea used clinically for type II diabetes, attenuated irradiation induced cell death in a concentration-dependent manner (12.5-200 µM) when administrated to cells 1-h prior to irradiation (FIG. 4A). Moreover, glyburide protected cells from irradiation induced apoptosis to a similar extent when administrated 30-min after γ-irradiation (FIG. 5A). Treatment of cells with 200 µM glyburide effectively protected cells from a wide range of irradiation exposure (5-25Gy) (FIG. 5B). The other nine chemicals lacked any obvious protective effect on γ-irradiation induced cell death under the current experimental conditions (FIG. 4A).

In Vitro Irradiation Survival Curves

The radioprotective effect of glyburide was further demonstrated by the in vitro clonogenic survival assay. Murine hematopoietic progenitor cell line 32D cl 3 was incubated with 10 µM glyburide for 1 h before irradiation (0-8 Gy) or by incubating the cells in methycellulose containing 10 µM glyburide following irradiation. Cells incubated in glyburide before irradiation demonstrated an increased radioresistance as seen by an increase in the n or shoulder on the irradiation survival curve of 34.9±0.5 compared to 3.1±1.3 or 2.5±0.9 (P=0.0018 or <0.0001, respectively) for 32D cl 3 cells alone or incubated with glyburide following irradiation (FIG. 6). There was no significant difference in the D0 for 32D cl 3 cells (1.14±0.20 Gy) compared to cells incubated in glyburide before or after irradiation (1.18±0.13 and 1.10±0.09 Gy, respectively).

In Vivo Survival Curves

C57BL/6NHsd female mice were injected intraperitoneally with 5 mg/kg glyburide either 10 min before or 10 min after 9.5 Gy total body irradiation. The mice were followed for the development of irradiation induced damage to the hematopoietic system which occurs within the first 30 days

TABLE 3

| Drugs/ Inhibitors | Target Gene Symbol | Gene Description | Location | Family |
|---|---|---|---|---|
| SB 203580 | MAPKAPK2 | Mitogen-activated protein kinase-activated protein kinase 2 | Nucleus | Kinase |
| Tyrphostin AG 112 | MST1R | Macrophage stimulating 1 receptor (c-met-related tyrosine kinase) | Plasma Membrane | Kinase |
| LY294002 | PAK4 | P21 (CDKN1A)-activated kinase 4 | Cytoplasm | Kinase |
| IMBX | PDE11A | Phosphodiesterase 11A | Cytoplasm | Enzyme |
| Rolipram | PDE4B | Phosphodiesterase 4B, cAMP-specific (phosphodiesterase E4 dunce homolog, *Drosophila*) | Cytoplasm | Enzyme |
|  | PDE4D | Phosphodiesterase 4D, cAMP-specific (Phosphodiesterase E3 dunce homolog, *Drosophila*) | Cytoplasm | Enzyme |
| Disulfiram | ALDH1A3 | Aldehyde dehydrogenase 1 family, member A3 | Cytoplasm | Enzyme |
| Glyburide | ABCA4 | ATP-binding cassette, sub-family A (ABC1), member 4 | Plasma Membrane | Transporter |
|  | ABCA8 | ATP-binding cassette, sub-family A (ABC1), member 8 | Plasma Membrane | Transporter |
|  | ABCC8 | ATP-binding cassette, sub-family C (CFTR/MRP), member 8 | Plasma Membrane | Transporter |
| Hexamethonium chloride | CHRNA1 | Cholinergic receptor, nicotinic, alpha 1 (muscle) | Plasma Membrane | Transmembrane receptor |
| Doxycycline hyclate | MMP9 | Matrix metallopeptidase 9 (gelatinase B, 92 kDa gelatinase, 92 kDa type IV collagenase) | Extracellular Space | Peptidase |
| Aprotinin | KLK5 | kallikrein 5 | Cytoplasm | peptidase |

Figure 5C:
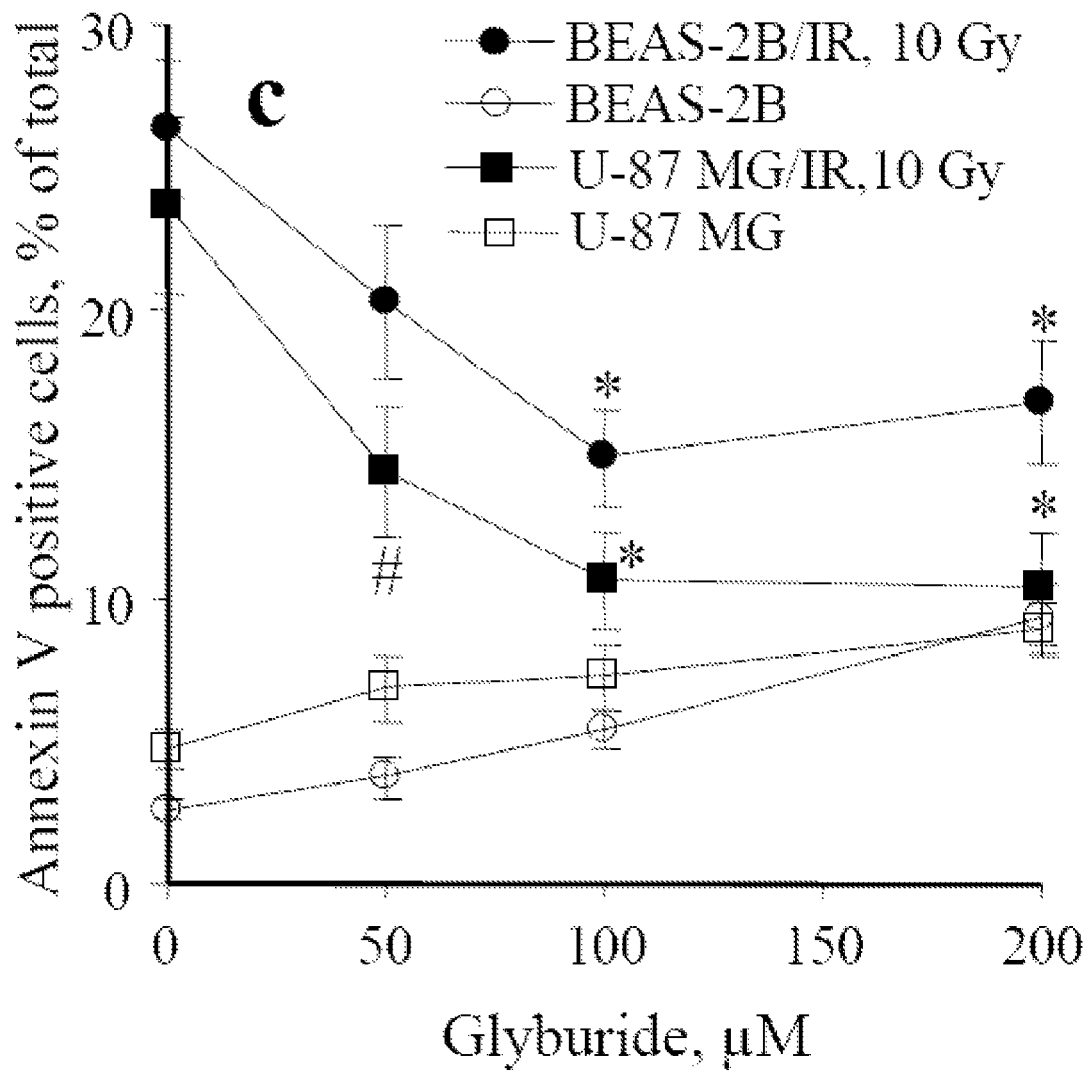
Figure 5D:
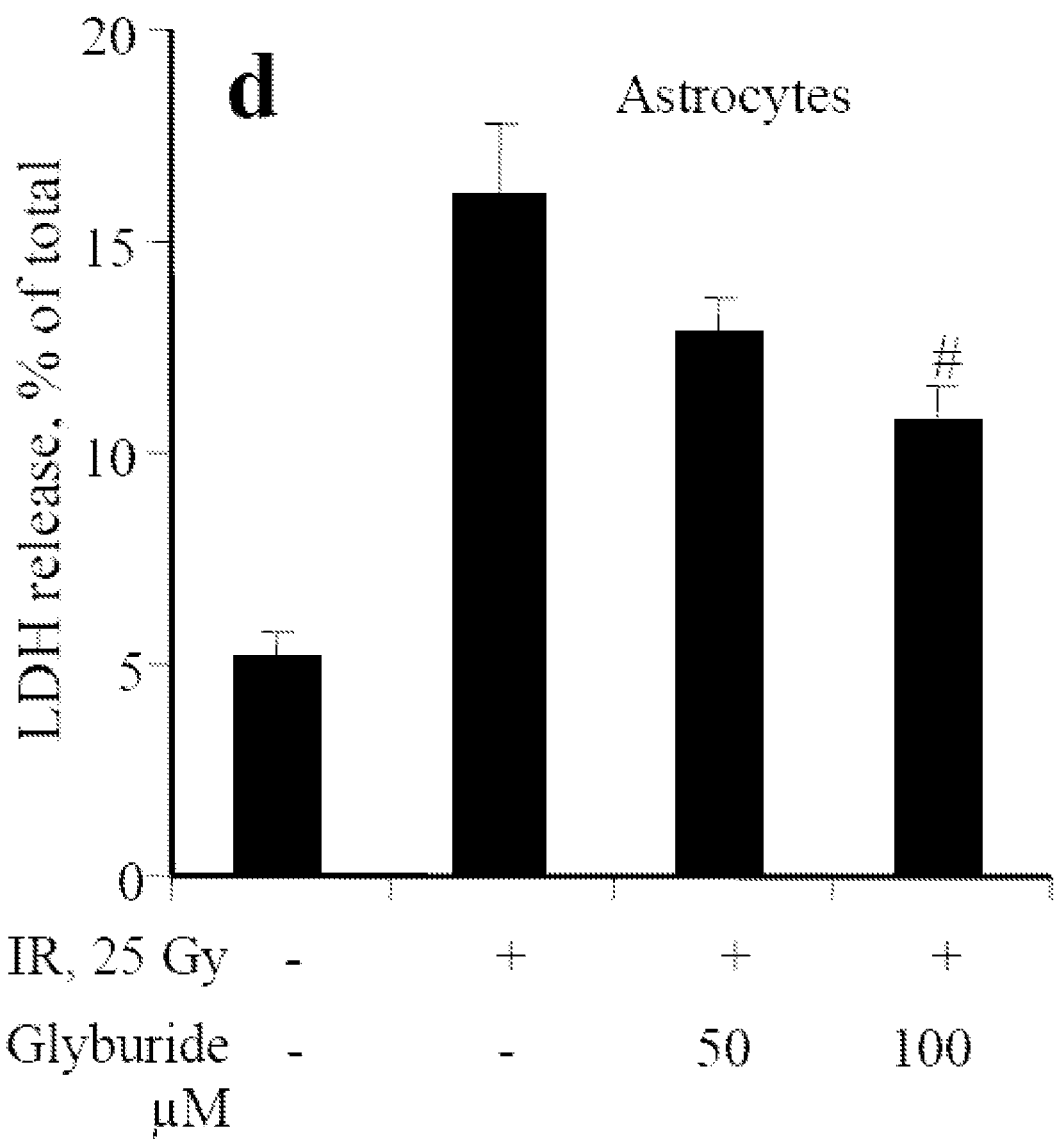

To further explore the radioprotective effect of glyburide, we extended the screening test to six other human histologically distinct cell lines: glioblastoma U-87 MG, cervical adenocarcinoma HeLa, lung carcinoma H1299, permanent bone marrow stromal KM101 and bronchial epithelial cells BEAS-2B, and human primary astrocytes. Cells were exposed to γ-irradiation at different doses (10 or 25 Gy) based on their radiosensitivity. We found that glyburide provided effective radioprotection in U-87 MG cells, BEAS-2B cells, and astrocytes (FIG. 5C, 5D). In contrast, glyburide exerted no protective effect on γ-irradiated H1299, HeLa, and KM101 cells under the current experimental setting (data not shown). The mechanisms responsible for the differences in glyburide response are not known but are worthy of further investigation.

after irradiation (FIG. 7). Mice injected with glyburide before irradiation were protected as seen by an increase in survival compared to the irradiated controls and mice injected with vehicle only (P=0.04). Mice injected with glyburide after irradiation, or with vehicle only were not protected from irradiation since their death rate was not changed in comparison to the irradiated control mice.

Discussion siRNA library screening affords an unbiased opportunity for large-scale and rapid target identification. It has been successfully employed to identify novel target for cancer therapeutics in transformed human cells (Zhang, B. et al. High-content fluorescent-based assay for screening activators of DNA damage checkpoint pathways. *J. Biomol. Screen* 13, 538-43 (2008) and Micklem, D. R. & Lorens, J. B. RNAi screening for therapeutic targets in human malignancies. *Curr. Pharm. Biotechnol.* 8, 337-343 (2007)), especially in a synthetic lethal format (Kaelin, W. G. Jr. The concept of synthetic lethality in the context of anticancer therapy. *Nat. Rev. Cancer* 5, 689-698 (2005)). However, there are no previous reports exploiting a synthetic protective strategy against ionizing radiation. In the present study, we exploited the synthetic protective siRNA screening concept to identify genes which, when silenced, protect human glioblastoma cells from ionizing radiation. Here we identified 116 potential radioprotective genes by screening a human druggable genome library. Only glyburide out of 10 candidate compounds demonstrated radioprotective effect in our cell-based screening model.

Specific mechanisms of the radioprotective action of glyburide have not been studied in this work. It is known, however, that sulfonylureas, including glyburide, act as ATP-sensitive potassium channel (such as ABCC8 in Table 3) blockers and are widely used in diabetes treatment (Johnson, B. F., Bhatia, C. K., Rzeszotarski, W. J. & Wolff, F. W. Preliminary clinical evaluation of glybenclamide in treatment of diabetes mellitus. *Diabetes* 19, 579-584 (1970) and Cox, R. W., Fergus, E. B., Henley, E. D. & Williams, R. H. Sulfonylureas and diabetes mellitus. I. Clinical evaluation. *Diabetes* 5, 358-365 (1956)). These applications are based on the interactions of glyburide with sulfonylurea receptor 1 (SUR1)— the regulatory subunit of the pancreatic KATP channel— essential for triggering insulin secretion via membrane depolarization (Simard, J. M., Woo, S. K., Bhatta, S. & Gerzanich, V. Drugs acting on SUR1 to treat CNS ischemia and trauma. *Curr. Opin. Pharmacol.* 8, 42-49 (2008)). It has also been reported that interactions of glyburide with sulfonylurea receptor 1 play a role in the regulation of apoptosis (Hambrock, A., de Oliveira Franz, C. B., Hiller, S. & Osswald, H. Glibenclamide-induced apoptosis is specifically enhanced by expression of the sulfonylurea receptor isoform SUR1 but not by expression of SUR2B or the mutant SUR1(M1289T). *J. Pharmacol. Exp. Ther.* 316, 1031-1037 (2006); Wang, L., Xu, D., Dai, W. & Lu, L. An Ultraviolet-activated K+ Channel Mediates apoptosis of Myeloblastic Leikemia cells. *J. Biol. Chem.* 274, 3678-3685 (1999); and Busija, D. W., Gaspar, T., Domoki, F., Katakam, P. V. & Bari, F. Mitochondrial-mediated suppression of ROS production upon exposure of neurons to lethal stress: Mitochondrial targeted preconditioning. *Adv. Drug Deliv. Rev.* (2008). [Epub ahead of print]). One possible mechanism is through regulatory effects of glyburide on ATP-sensitive potassium channels, which participate in the regulation of apoptosis by controlling intracellular $Ca^{2+}$ level and affecting the mitochondrial permeability transition pore (Busija, D. W., et al. *Adv. Drug Deliv. Rev.* (2008). [Epub ahead of print] and Mozaffari, M. S. & Schaffer, S. W. Effect of pressure overload on cardioprotection of mitochondrial KATP channels and GSK-3beta: interaction with the MPT pore. *Am. J. Hypertens.* 21, 570-575 (2008)). Indeed, several drugs, including glyburide, have been shown to act as regulators of this channel, hence affect execution of apoptotic program (Busija, D. W., et al. *Adv. Drug Deliv. Rev.* (2008). [Epub ahead of print] and Miura, T. & Miki, T. ATP-sensitive $K^+$ channel openers: old drugs with new clinical benefits for the heart. *Curr. Vasc. Pharmacol.* 1, 251-258 (2003)). Currently, we are testing other potassium channel inhibitors in our cell-based model for their radioprotective effects.

Alternatively, the radioprotective effect of glyburide may be realized through interaction with other potential targets. For instance, we demonstrated here that siRNA knock down of ABCA4 and ABCA8

ATP-binding cassettes members, sub-family A, member 4 and 8 conferred radioprotective effect in T98G cells. However, little information exists in the current literature about the potential involvement of these two gene products in the apoptotic signaling pathway. The fact that glyburide afforded only limited protection of irradiated H1299, HeLa and KM101 cells indicates that the radioprotective effect of glyburide is cell type specific and this is worthy of further study. The results may also indicate that the SV40-immortalized human marrow stromal cell line KM101, and tumor cell lines tested may display heterogeneous radiation response modulation by glyburide associated with varying properties of the transformed phenotype. Since irradiated growth factor dependent, non-tumorigenic 32D cl 3 cells as well as total body irradiated mice were radioprotected by glyburide, this result may indicate that there is a more uniform normal tissue specific radioprotection.

Our proof of principle findings demonstrate the usefulness of druggable genome synthetic protective siRNA library screening for identifying novel radioprotectors and mitigators from existing drugs by combining a high-throughput protocol with conventional pharmacological assays. Glyburide is an orally active, safe, clinically used drug to treat type 2 diabetes. The maximal tolerated dose of glyburide has been established as 10 mg, twice daily, in patients <65 yr of age, or half the dose, 10 mg, daily, in patients > or =65 yr of age) (Peters, A. L. & Davidson, M. B. Maximal dose glyburide therapy in markedly symptomatic patients with type 2 diabetes: a new use for an old friend. *J. Clin. Endocrinol. Metab.* 81, 2423-2427 (1996)). In our study, we found that glyburide (pre-irradiation treatment) significantly increased the shoulder on the irradiation survival curve in 32D cl 3 cells. Most importantly, glyburide (pre-irradiation treatment) at a dose of 5 mg/kg increased the survival rate of C57BL/6NHsd female mice subjected to 9.5 Gy total body irradiation. It is known that all sulfonylurea drugs, including glyburide, are capable of producing severe hypoglycemia (Feldman, J. M. Review of glyburide after one year on the market. *Am. J. Med.* 79, 102-108 (1985) and Feldman, J. M. Glyburide: a second-generation sulfonylurea hypoglycemic agent. History, chemistry, metabolism, pharmacokinetics, clinical use and adverse effects. *Pharmacotherapy* 5, 43-62 (1985)). In the present study, we found that the dose of glyburide used did not cause hypoglycemia.

Glyburide effectively blocked irradiation induced apoptosis in a cell-based screen, and as shown in FIGS. 5A and 7, appears to mitigate the effects of radiation exposure if administered after irradiation. It is likely that other types of non-apoptotic types of cell death, such as mitotic catastrophe, necrosis, autophagy and senescence, are involved in the irradiation-induced damage. We are currently developing different screening strategies (e.g., cells transfected post-irradiation) focusing on the development of radiation mitigators.

Overall, our results demonstrate the power of unbiased siRNA screening with a druggable genome library and suggest that glyburide might be a clinically useful radioprotector.

Having described this invention above, it will be understood to those of ordinary skill in the art that the same can be performed within a wide and equivalent range of conditions, formulations and other parameters without affecting the scope of the invention or any embodiment thereof. Any document incorporated herein by reference is only done so to the extent of its technical disclosure and to the extent it is consistent with the present application and the disclosure provided herein.

We claim:

1. A method of reducing, preventing, or mitigating radiation injury in a subject, comprising administering to the subject prior to, during or after exposure of the subject to radiation, an amount of a sulfonylurea hypoglycemic effective to reduce, prevent, or mitigate radiation injury in the subject, wherein the sulfonylurea hypoglycemic compound is chosen from one or more of glyburide, acetohexamide, tolazamide, tolbutamide, glipizide, gliclazide, gliquidone, glyclopyramide, and glimepiride.

2. The method of claim 1, wherein the radiation is ionizing radiation.

3. The method of claim 1, wherein the sulfonylurea hypoglycemic is glyburide.

4. The method of claim 3, wherein between 0.1 mg to 20 mg of glyburide is administered to the subject one to ten times in per day.

5. The method of claim 4, wherein the glyburide is administered as an oral dosage form in an amount ranging from 1.25 mg to 6.0 mg per dose.

6. The method of claim 4, wherein the glyburide is administered parenterally in an amount ranging from 0.1 mg to 20.0 mg per dose.

7. The method of claim 1, wherein the compound is administered to the subject in an amount effective to produce a blood concentration of the sulfonylurea hypoglycemic in the subject ranging from 1 µM to 25 µM.

8. The method of claim 1, wherein from 0.1 mg to 20 mg of the sulfonylurea hypoglycemic is administered to the subject per day.

* * * * *

UNITED STATES PATENT AND TRADEMARK OFFICE
CERTIFICATE OF CORRECTION

PATENT NO. : 8,883,852 B2  
APPLICATION NO. : 13/124924  
DATED : November 11, 2014  
INVENTOR(S) : Michael W. Epperly et al.

Page 1 of 1

It is certified that error appears in the above-identified patent and that said Letters Patent is hereby corrected as shown below:

On the Title Page

Column 1, Item (73) Assignee, Line 1, delete "Pittburgh" and insert -- Pittsburgh --

Column 2, Item (56) OTHER PUBLICATIONS, Line 20, delete "CI" and insert -- CL --

Column 2, Item (56) OTHER PUBLICATIONS, Line 31, delete "Stabiliization" and insert -- Stabilization --

Column 2, Item (56) OTHER PUBLICATIONS, Line 40, delete "cI" and insert -- cl --

Signed and Sealed this  
Fourteenth Day of April, 2015

Michelle K. Lee  
*Director of the United States Patent and Trademark Office*